United States Patent
Hardin et al.

(10) Patent No.: US 10,300,158 B2
(45) Date of Patent: May 28, 2019

(54) DATA COLLECTION DEVICE WITH ANTI-MICROBIAL ILLUMINATION

(71) Applicant: Datalogic USA Inc., Eugene, OR (US)

(72) Inventors: Wesley W. Hardin, Eugene, OR (US); Matt Monte, Eugene, OR (US); Ryan Thompson, Eugene, OR (US)

(73) Assignee: Datalogic USA Inc., Eugene, OR (US)

( * ) Notice: Subject to any disclaimer, the term of this patent is extended or adjusted under 35 U.S.C. 154(b) by 0 days.

(21) Appl. No.: 15/852,252

(22) Filed: Dec. 22, 2017

(65) Prior Publication Data

US 2019/0070324 A1     Mar. 7, 2019

Related U.S. Application Data

(63) Continuation-in-part of application No. 15/696,007, filed on Sep. 5, 2017.

(51) Int. Cl.
| | |
|---|---|
| G06K 7/10 | (2006.01) |
| G06K 15/12 | (2006.01) |
| A61L 2/10 | (2006.01) |
| F21V 23/04 | (2006.01) |
| G06T 7/73 | (2017.01) |
| F21V 23/00 | (2015.01) |

(52) U.S. Cl.
CPC .............. *A61L 2/10* (2013.01); *F21V 23/003* (2013.01); *F21V 23/0471* (2013.01); *G06T 7/73* (2017.01); *A61L 2202/14* (2013.01)

(58) Field of Classification Search
USPC .................. 235/462.41, 462.01, 462.45, 235/472.01–472.03
See application file for complete search history.

(56) References Cited

U.S. PATENT DOCUMENTS

| | | | |
|---|---|---|---|
| 8,297,435 | B2 | 10/2012 | Lathem |
| 8,398,264 | B2 | 3/2013 | Anderson et al. |
| 9,039,966 | B2 | 5/2015 | Anderson et al. |
| 9,572,901 | B2 | 2/2017 | Todeschini |
| 9,700,641 | B2 | 7/2017 | Hawkins et al. |
| 2011/0290889 | A1* | 12/2011 | Tamburrini ........ G06K 7/10881 |
| | | | 235/470 |
| 2015/0071819 | A1* | 3/2015 | Todeschini ............ A61L 2/0052 |
| | | | 422/24 |

(Continued)

OTHER PUBLICATIONS

De Lucca, A.J., et al., "Blue light (470 nm) effectively inhibits bacterial and fungal growth," Letters in Applied Microbiology 55, 460-466.

(Continued)

*Primary Examiner* — Tuyen K Vo
(74) *Attorney, Agent, or Firm* — Dentons US LLP

(57) ABSTRACT

A code reader may include a housing configured to be adjustably oriented. The housing may include at least one orientation corresponding with a cleaning function. A scanner may be disposed within the housing, and be configured to scan a machine-readable indicia in a target area. An illumination source may be configured to emit an anti-microbial illumination. A processing unit may be in communication with the scanner and illumination source, and be configured to select the cleaning function to cause the illumination source to emit the anti-microbial illumination toward the target area to disinfect surfaces in the target area.

21 Claims, 16 Drawing Sheets

(56) References Cited

U.S. PATENT DOCUMENTS

2016/0271659 A1* 9/2016 Russ .................. A61B 7/00
2017/0296686 A1* 10/2017 Cole .................. A61L 2/10

OTHER PUBLICATIONS

Indigo-Clean, www.kenall.com/home/products/indigo-clean, printed Dec. 22, 2017, 6 pages.
VioSafe Antibacterial White LED Products, www.vitalvio.com/products, printed Dec. 22, 2017, 7 pages.

* cited by examiner

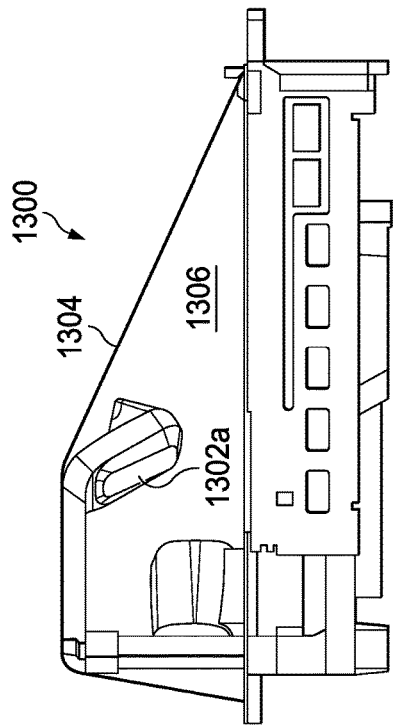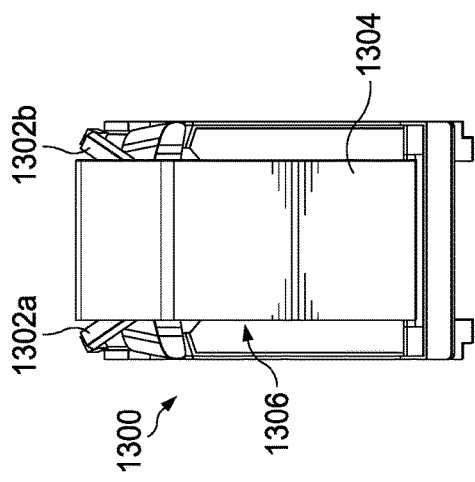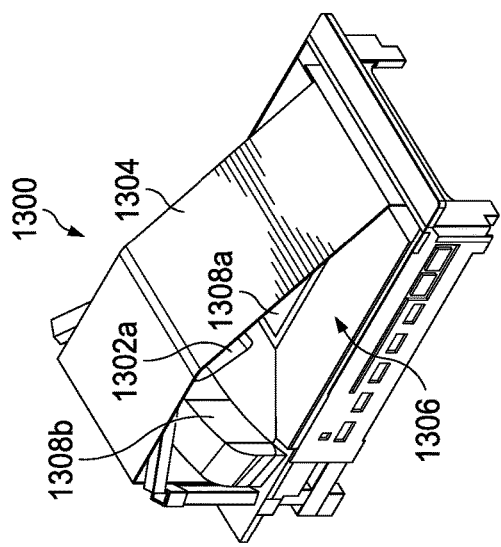

DATA COLLECTION DEVICE WITH ANTI-MICROBIAL ILLUMINATION

RELATED APPLICATIONS

This application is a continuation-in-part of co-pending U.S. application Ser. No. 15/696,007 filed Sep. 5, 2017 and entitled "Automated Modification Of Imaging Scanner Function Based On Orientation:" the contents of which are hereby incorporated by reference in their entirety.

FIELD OF THE INVENTION

The present invention relates to barcode readers, and more specifically, to barcode readers having a cleaning or disinfecting function for disinfecting surfaces of workspaces.

BACKGROUND OF THE INVENTION

Barcode readers are used in a variety of venues. The purpose of a barcode reader can vary greatly from venue to venue as well as within the venue. In retail environments, a venue may have multiple barcode readers at a single station or point-of-sale for performing various functions. For example, a venue may have a first barcode reader for scanning barcodes on products, a second barcode scanner for reading checks and other forms of payment, and a third barcode reader for identifying objects in a basket. Each barcode reader provides different functions that use different configurations, such as illumination, field-of-view, and reading capabilities. It should be understood that barcode readers are capable of reading machine-readable indicia other than barcodes, including two-dimensional codes, such as QR codes.

Moving a single barcode reader from one orientation to another is time and resource intensive as a user often has to manually modify each of the settings affected by the new orientation and related functionality. Time and personnel are valuable resources to meet demand. As a result, venues install multiple barcode readers with a purpose of each barcode reader stationary in its orientation (or be dedicated to being operated in a hand-held mode), thus removing the need to ever change settings and functionality. Even though the use of multiple barcode readers is less costly in time and personnel resources, the cost of obtaining and maintaining extra barcode readers is a burden on the venue.

Barcode readers are often used within environments in which harmful germs and bacteria exist. For example, barcode readers are used in grocery stores in which foods and chemicals are placed on scanning or processing areas (e.g., workspace surfaces) at the barcode readers. As another example, barcode readers are used in hospitals and other environments in which harmful germs and bacteria exist. As an example, in a grocery store, food products, such as chicken grease, may contact a work surface, such as a conveyer belt, barcode scanner surface, or other surface. As such, reducing harmful germs and bacteria in food handling applications, hospitals, and other environments is highly desirable. Currently, cleaning chemicals and expensive anti-microbial materials are used to control/clean the scanning areas or workspace surfaces, including user interfaces, at the barcode readers. The workspace surfaces could be cleaner, safer, and more efficient while reducing the use of expensive and potentially harmful chemicals. Many of the chemicals that are used to disinfect surfaces are harmful and/or degrade materials (e.g. polycarbonate/ABS) commonly found in the workspace.

BRIEF SUMMARY OF THE INVENTION

A barcode or code reader may be configured to automatically adjust at least one setting in order to perform a functionality corresponding to a detected orientation of the barcode reader. In response to a sensor sensing a new orientation, the barcode reader may automatically select a corresponding function. The automatic selection of a function according to orientation may be performed in real time so that a process performed by the barcode reader and corresponding workstation may have limited, or no, interruption of operation. The barcode reader may be connected to a stand of a workstation or barcode reader system of a point-of-sale (POS) so that orientation is determined based on a configuration of a housing of the barcode reader. The housing may be detachably connected to the stand so that detaching of the barcode reader indicates a hands-free mode of operation. In an alternative embodiment, rather than being responsive to a change in orientation, the barcode reader may determine orientation in response to a request or activation of a reading function and adjust functionality and/or settings at that time based on the determined orientation. Orientation may alternatively be determined based on trained image position sensing in which analysis of the background of the imager's current field-of-view determines function of the scanner based on a comparison of pre-established images set during a "training" mode in which specific behavior is established in relationship to an image background (e.g., top surface of a scanner system).

One orientation may correspond with a cleaning function. The cleaning function may include emitting an anti-microbial illumination that is used to clean or disinfect surface(s) onto which the barcode scanner illuminates with the anti-microbial illumination. The anti-microbial illumination is an illumination with a wavelength that causes microbes (e.g., bacteria) to be deactivated or killed. The cleaning function may correspond with more than one orientation, and may include emitting (i) a first power level of the anti-microbial illumination to coincide with emitting an illumination for reading a barcode in a first orientation and (ii) a second power level of the anti-microbial illumination in a second orientation for higher intensity cleaning, where the first power level may be lower than the second power level. Additionally and/or alternatively, the anti-microbial illumination may be turned on automatically, semi-automatically, and/or manually on a periodic (e.g., once or more times per day) or aperiodic (e.g., in response to an event, such as a protection screen being pulled over a surface area on which the barcode scanner is configured to illuminate with the anti-microbial illumination). In addition to the anti-microbial illumination being produced by an illuminator (e.g., LED illumination between approximately 380 and about 470 nm wavelengths that produce blue light) of the barcode scanner, illumination devices (e.g., LEDs) may be disposed on poles or light fixtures arranged to illuminate the surface(s) with the anti-microbial illumination at which the barcode scanner operates.

One embodiment of a code reader may include a housing configured to be adjustably oriented. The housing may include at least one orientation corresponding with a cleaning function. A scanner may be disposed within the housing, and be configured to scan a machine-readable indicia in a target area. An illumination source may be configured to emit an anti-microbial illumination. A processing unit may be in communication with the scanner and illumination source, and be configured to select the cleaning function to cause the illumination source to emit the anti-microbial illumination toward the target area to disinfect surfaces in the target area.

One embodiment of a method for disinfecting a target area at a code reader may include determining if an orientation of a housing inclusive of a scanner for reading machine-readable indicia is an orientation corresponding with a cleaning function. In response to determining that the orientation of the housing is the orientation corresponding with the cleaning function, a cleaning function may be selected to cause an anti-microbial illumination to be emitted toward a target area of the scanner.

One embodiment of a method for disinfecting a surface at a code reader may include sensing an environmental factor at the code reader. In response to determining that the environmental factor is at a first value, the code reader may be configured to read machine-readable indicia. In response to determining that environmental factor is at a second value, an anti-microbial illumination may be caused to be emitted toward a target area of the scanner.

BRIEF DESCRIPTION OF THE DRAWINGS

Illustrative embodiments of the present invention are described in detail below with reference to the attached drawing figures, which are incorporated by reference herein and wherein:

FIGS. 13A-13C are illustrations of an illustrative code reader inclusive of a reflective roller shade for use in a cleaning function;

DETAILED DESCRIPTION OF THE INVENTION

Figure 1:
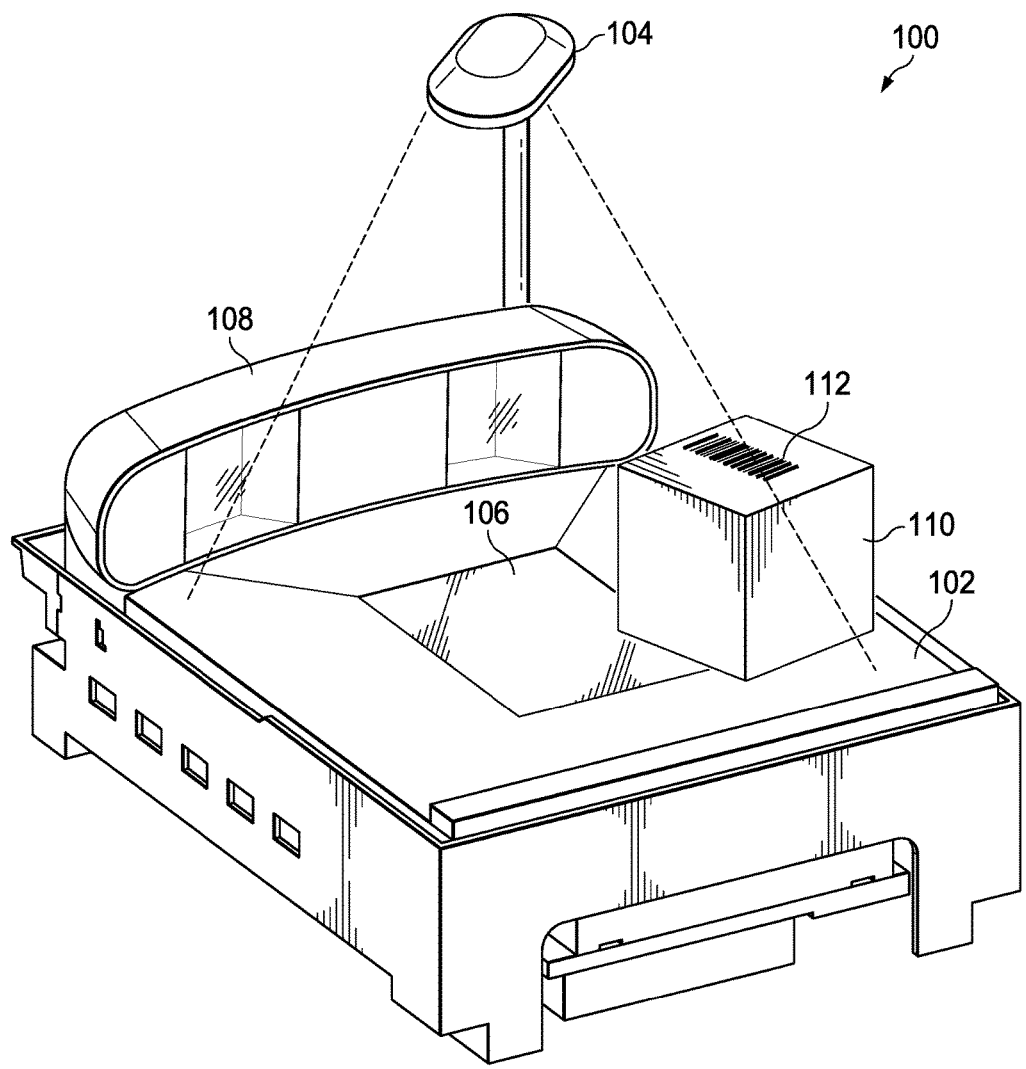
FIG. 1 is an illustration of an illustrative barcode reader system configured to read machine-readable indicia utilizing a code reader inside a housing having a set of orientations.

With regard to FIG. 1, an illustration of a barcode reader system 100 including a base 102 and code reader 104 configured to read machine-readable indicia is shown. The code reader 104 may be configured to be positioned in multiple orientations. The barcode reader system 100 may further include a first barcode scanner 106, and a second barcode scanner 108 to enable the barcode reader system 100 to read machine-readable indicia from three different angles to provide efficiency in reading a machine-readable indicia on an object, such as a consumer package. The barcode reader system 100 may be configured to identify item 110 by reading a machine-readable indicia 112 in a target area within a field-of-view of the barcode reader system 100. The machine-readable indicia 112 may be representative of a code (e.g., UPC code) associated with the item 110 that enables the barcode reader system 100 to identify the items for checkout at a store or other purpose. "Barcode" may refer to a "barcode," "code," or any other machine-readable indicia as known by one of skill in the art.

In one embodiment, the barcode reader system 100 may be configured to constantly scan the target area, such as, but not limited to, a scanning station. In response to identifying the existence of an item 110 in the target area, the first and second barcode scanners 106 and 108 and the code reader 104 may scan or image the machine-readable indicia 112 (e.g., barcode, QR code, or any other machine-readable code or markings) captured on the item 110. The barcode reader system 100 may have a variety of alternative configurations, as understood in the art.

Figure 2:
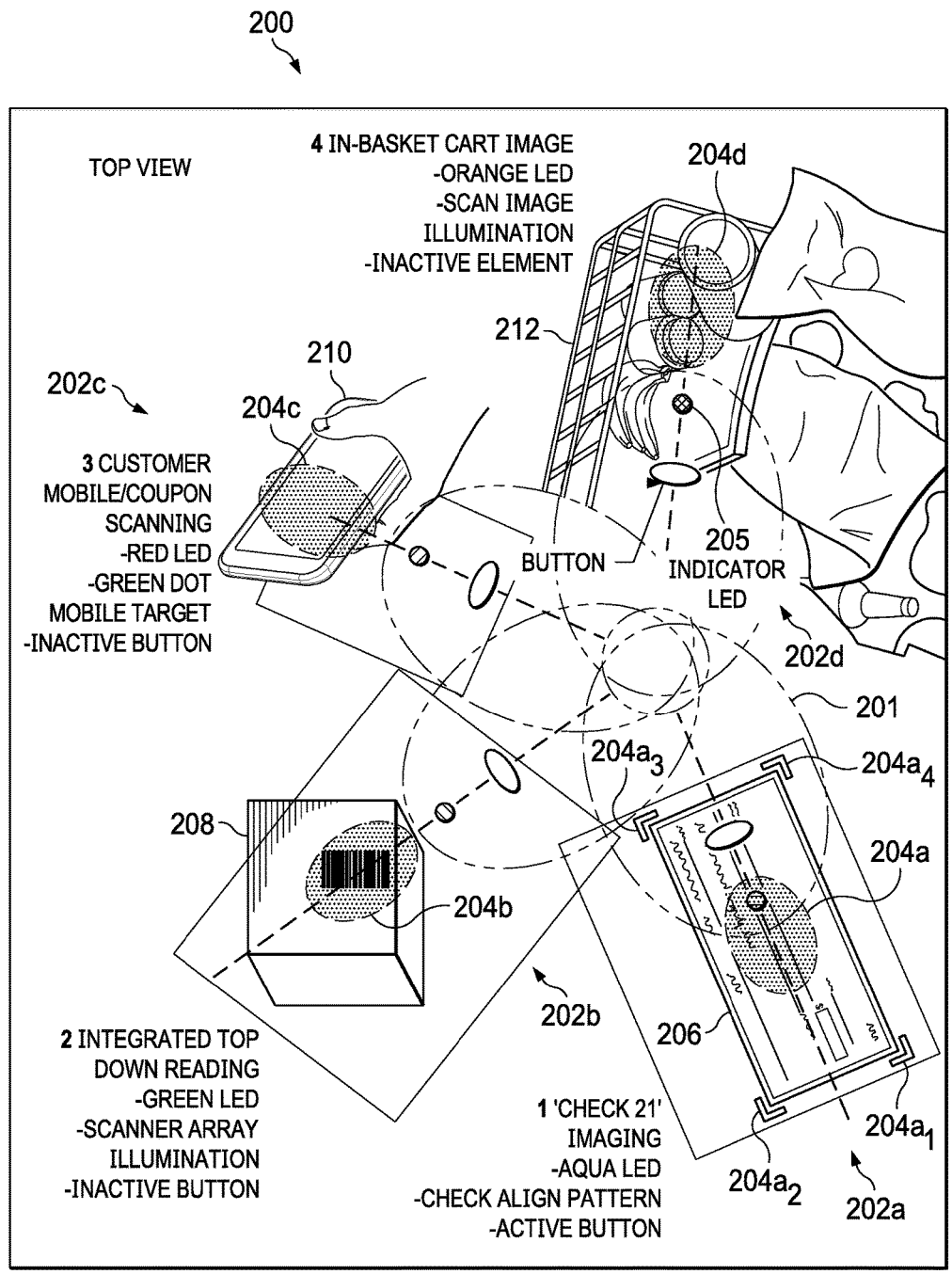
FIG. 2 is an illustration of an illustrative housing of a code reader in four different orientations.

With regard to FIG. 2, an illustration of a barcode reader 200 having a housing 201 of a code reader is shown in four different mutually different orientations 202a-202d (collectively 202). In one embodiment, the housing 201 includes a light source (not shown) that may illuminate a target area. In one embodiment, the housing 201 may include a target indicator light (not shown) that may provide a positioning spot or other indicator (e.g., rectangle corners $204a_1$-$204a_4$ (collectively 204a) 204a-204d (collectively 204) to indicate to a user where to place an item for reading. If different target indictor lights are used to support different functions of the barcode reader 104, then the barcode reader 104 may include a driver system (e.g., processor, optical source driver, etc.) to automatically select and control the appropriate light source(s) to turn on and off the light source(s) based on the selected function. In addition to a light source, a function indicator light 205 may be used to notify a user of the selected function. In one embodiment, the indicator light 205 may produce different colors (e.g., red, green, blue, violet), and each function may cause the function indictor light 205 to produce a different color. Alternatively, the function indicator light 205 may be composed of multiple lighting elements associated with different physical positions on the housing 201 to indicate different functions.

To operate the barcode scanner 200, the scanner 200 may be set to an automatic scan mode to continuously scan, scan in response to an event (e.g., identification of motion), periodically scan (e.g., scan every 0.1 seconds), or manually scan in response to a user pressing a button 207 to initiate a scan. In response to pushing the button 207, the scanner 200 may automatically determine a function based on orientation (e.g., angular, inclination, motion, background image content) of the scanner 200. Alternatively, the scanner 200 may be configured for a particular function based on orientation prior to a user pushing the button 207 (e.g., in response to a change in orientation, the scanner changes function, thereby being configured to a particular function prior to activation of a scan request by a user or automatic scanning, as previously described).

The barcode reader 200 may include different functions corresponding to the respective four orientations 202 of the housing 201. The functions may be automatically selected by adjusting at least one setting of the barcode reader 200. The settings may include, but are not limited to, depth of field, region of interest, type of data captured, type and format of data transmitted (e.g., fully decoded barcode data in a case of a customer facing scanner function versus time-synced frame contents in the case of a top-down reader, and non-synced images in a case of an in-basket scanner and check imager, such as a Check 21 imager). Transition from one function to another may be achieved dynamically in real-time or near-real-time so that transmission from the code reader is seemingly, or actually, instantaneous to avoid usage disruption or delay.

Figure 5:
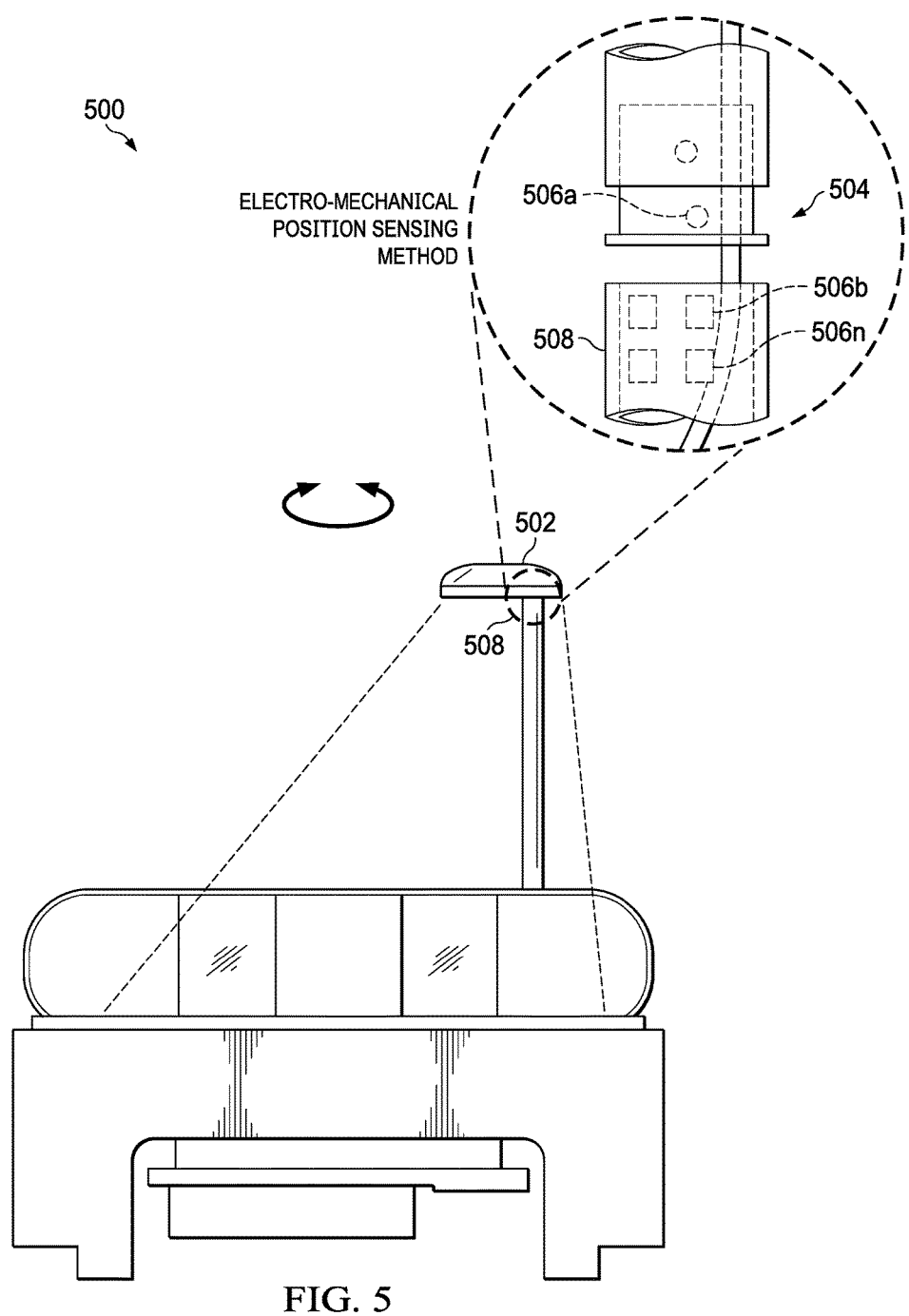
FIG. 5 is an illustration of an illustrative barcode reader system having a code reader inclusive of an electromechanical sensor used to determine orientation.
Figure 9:
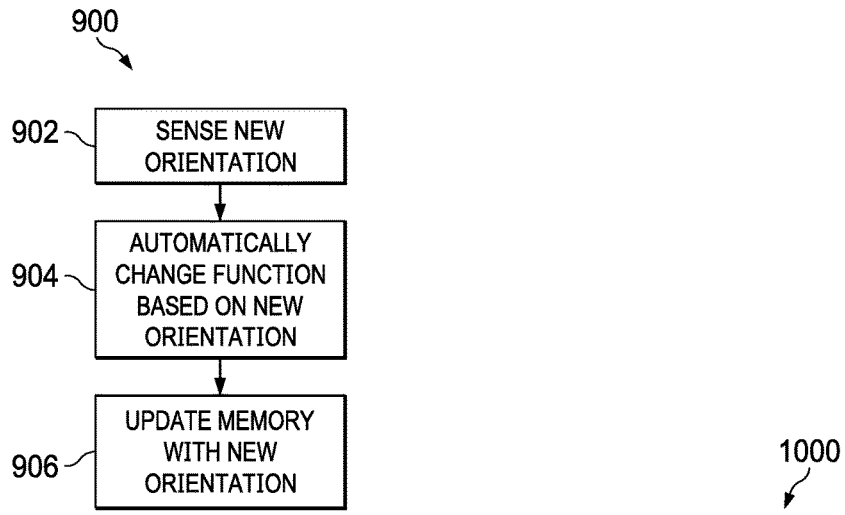
FIG. 9 is a flow diagram of an illustrative method of automatically selecting a function of a code reader based on an orientation thereof.
Figure 10:
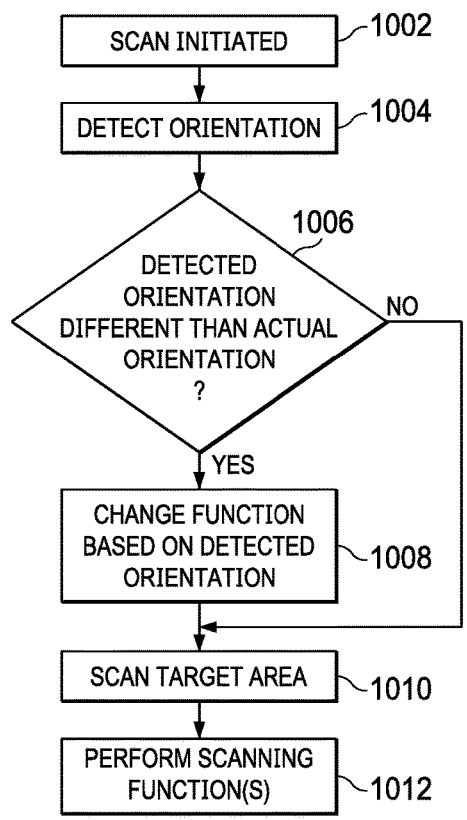
FIG. 10 is a flow diagram of an illustrative method of automatically selecting a function of a code reader based on an orientation thereof.

The barcode reader 200 may automatically change functions in response to a change in orientation of the housing 201. In one embodiment, a change in orientation is sensed by at least one electromechanical sensor, such as shown in FIGS. 5 and 9, and communicated to the barcode reader 200 so that the barcode reader 200 may automatically select a function corresponding to the orientation of the housing 201. In one embodiment, a scan may initiated, such as shown in FIG. 10, and the orientation of the housing 201 may be determined initially by an image captured of a background portion of the target area. For example, determining an orientation of the housing 201 based on the image of the target area may include identifying known features (e.g., scanning window or a base of a barcode scanner system) in a background portion of the image of the target area that correspond with a function corresponding with the orientation of the housing 201. The barcode reader 200 is shown in four orientations 202 as an example, and an alternative number of orientations corresponding with different functions may be supported.

A first orientation 202*a* of the housing 201 may be a check imaging orientation. A function of the barcode reader 200 in the check imaging orientation may be an imaging function. The barcode reader 200 may capture an image of a check 206 that a user has placed in the target area. In an embodiment, the barcode reader 200, in response to the barcode reader 200 entering into a check imaging function, one or more illumination devices may be turned on to define a region in which a check (or other item) may be placed. The illumination devices may define a rectangle in which the check is to be placed, for example, thereby supporting specific functionality of processing checks, which generally has a higher degree of image processing than barcode scanning. The imaging function may include auto-sizing and meeting pixel requirements for check processing applications, such as, for example, Check 21 processing. The imaging function may include parallax corrections as well as other imaging corrections for reading and verifying checks known to one of skill in the art.

In one embodiment, the orientations 202 may be determined by angular or other (e.g., inclination) orientation of the housing 201. In another embodiment, the orientations may be determined by identifying a background portion (e.g., outline on a base, sticker, text, or other fixed feature in the target area). Orientation may be determined by a variety of alternative methods, as further described herein.

A second orientation 202*b* of the housing 201 may be a barcode scanner orientation. A function of the barcode reader 200 in the barcode scanner orientation 202*b* may be to constantly, periodically, or aperiodically scan the target area. In response to identifying an item 208 in the target area, the code reader may scan or image a machine-readable indicia disposed on the item 208. The barcode reader 200 may communicate the image to a POS system optionally to be processed with images captured by additional scanners below and to a side of the item 208 (see FIG. 1, for example). The barcode reader 200 may also be configured to identify a code associated with the item 208 by reading the machine-readable indicia and communicating the code associated with the item 208 to an external processing unit (e.g., POS system). Orientation of the housing 201 may be determined by at least those methods as described hereinabove with reference to the check imaging orientation as well as identifying a machine-readable indicia in the target area.

A third orientation 202*c* of the housing 201 may be a mobile device reader orientation for reading a machine-readable indicia displayed on a screen of a mobile device 210. A function of the barcode reader 200 in the mobile device reader orientation 202*c* may be image processing that has different settings than those used to read barcodes on items. The barcode reader 200 may read or capture an image on the mobile device 210. The barcode reader 200 may then transmit the image to an external processing unit. The barcode reader 200 may provide a positioning spot 204*c* to indicate to a user where to place the mobile device 210 to optimize reading the screen of the mobile device 210. The screen of the mobile device 210 may display an image of a number of illustrative items related to point-of-sale transactions, such as, but not limited to, coupons, payment information, venue membership information, and other items known to those of skill in the art for use in purchasing or paying for items. Orientation may be determined by at least those methods as described hereinabove with reference to the check imaging orientation as well as identifying a mobile device or an illuminated screen in the target area.

A fourth orientation 202*d* of the housing 201 may be an in-basket orientation for scanning contents of a basket 212. A function of the barcode reader 200 in the in-basket orientation 202*d* may be image processing as well as changing a focal distance or field-of-view settings or parameters of the barcode reader 200. The barcode reader 200 may capture and process images of the basket 212 to determine a variety of parameters, such as, but not limited to, how many items remain in the basket 212, if any items are hidden underneath other items in the basket 212, how many of a same item are in the basket 212 to speed up check-out time, and other parameters known to those with skill in the art.

A fifth orientation (not shown) of the housing 201 may be a cleaning orientation for cleaning the barcode reader 200.

A function of the barcode reader 200 in the cleaning orientation may be a cleaning function including cleaning working surfaces and scanners of the barcode reader 200. The housing 201 may be configured to emit an anti-microbial illumination during the cleaning function and may be described in further detail hereinbelow with regard to FIGS. 11A-18. The cleaning function may also correspond with the first orientation 202a, the second orientation 202b, and the third orientation 202c in addition to, or independent of, the fifth orientation.

Figure 3:
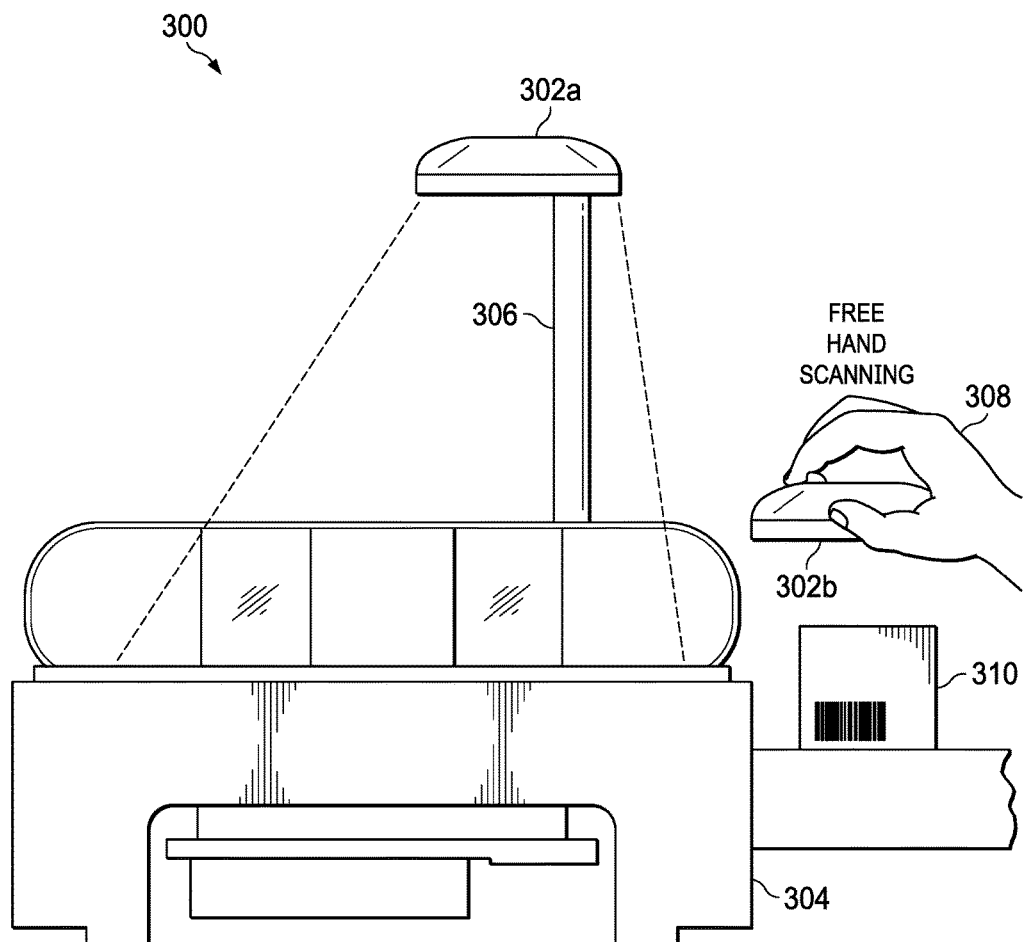
FIG. 3 is an illustration of an illustrative code reader in a fifth orientation, which is a handheld scanning orientation.

With regard to FIG. 3, an illustration of a barcode reader system 300 having a barcode reader 302a and 302b (collectively 302) in a handheld scanning orientation 303 is shown. The barcode reader system 300 may include a base 304 that may operate as a portion of a POS, and to which a support stand 306 may be connected. The barcode reader 302 may be detached, by a user 308, from the support stand 306 for use in a handheld reading function mode. The barcode reader 302b in the handheld reading function mode may allow the user 308 to scan or image an item 310 that is not within a field-of-view of the code reader 302a in an attached orientation when positioned on the support stand 306.

In one embodiment, a function of the code reader 302 in the handheld scanning orientation 303 may be image processing and data storage. The code reader 302 may be configured to scan a target area for an item inclusive of a machine-readable indicia. In one embodiment, the barcode reader 302b in a handheld reading function mode may transmit an image of the target area back to the base 304, for example, a point-of-sale station, through a wireless communication system, such as, but not limited to, WiFi®, Bluetooth®, NFC®, wired, or other communication methods known to those of skill in the art.

In another embodiment, the barcode reader 302b in the handheld mode may store any gathered information from the item 310 in local memory. In an embodiment, the locally stored data may be transmitted to the base 304 when the code reader 302b is re-attached to the support stand 306. The stored data may include product information, venue information read from a barcode (e.g., UPC barcode), item count, item sizes, images, OCR data, as well as other data relevant to consumer goods.

The handheld scanning orientation 303 may be determined by any of the processes described hereinabove with reference to FIG. 2, as well as other methods one of skill in the art will appreciate with regard to handheld devices. For example, in one embodiment, orientation may be determined by a gravimeter disposed within a housing of the barcode reader 302. Alternatively and/or additionally, accelerometer(s) to sense motion, inclinometer to sense inclination, or other motion or orientation sensor may be utilized. In one embodiment, the barcode reader 302 may sense detachment from the base 304. In one embodiment, a power feed may be disconnected at detachment and the barcode reader 302 may sense a lack of power feed and/or beginning to use power local to the barcode reader 302, such as, but not limited to, a battery, a capacitor, a set of capacitors, a super capacitor, or any other power supply method known to those of skill in the art. A motion or other sensor may alternatively be used to sense that the barcode reader 302 is in a handheld scanning orientation 303. In an embodiment, a determination that the barcode reader 302 is in the orientation 303 may be performed in response to being detached from the support stand 306, in response to being moved, or commanded to perform a scan, as further described herein.

Figure 4:
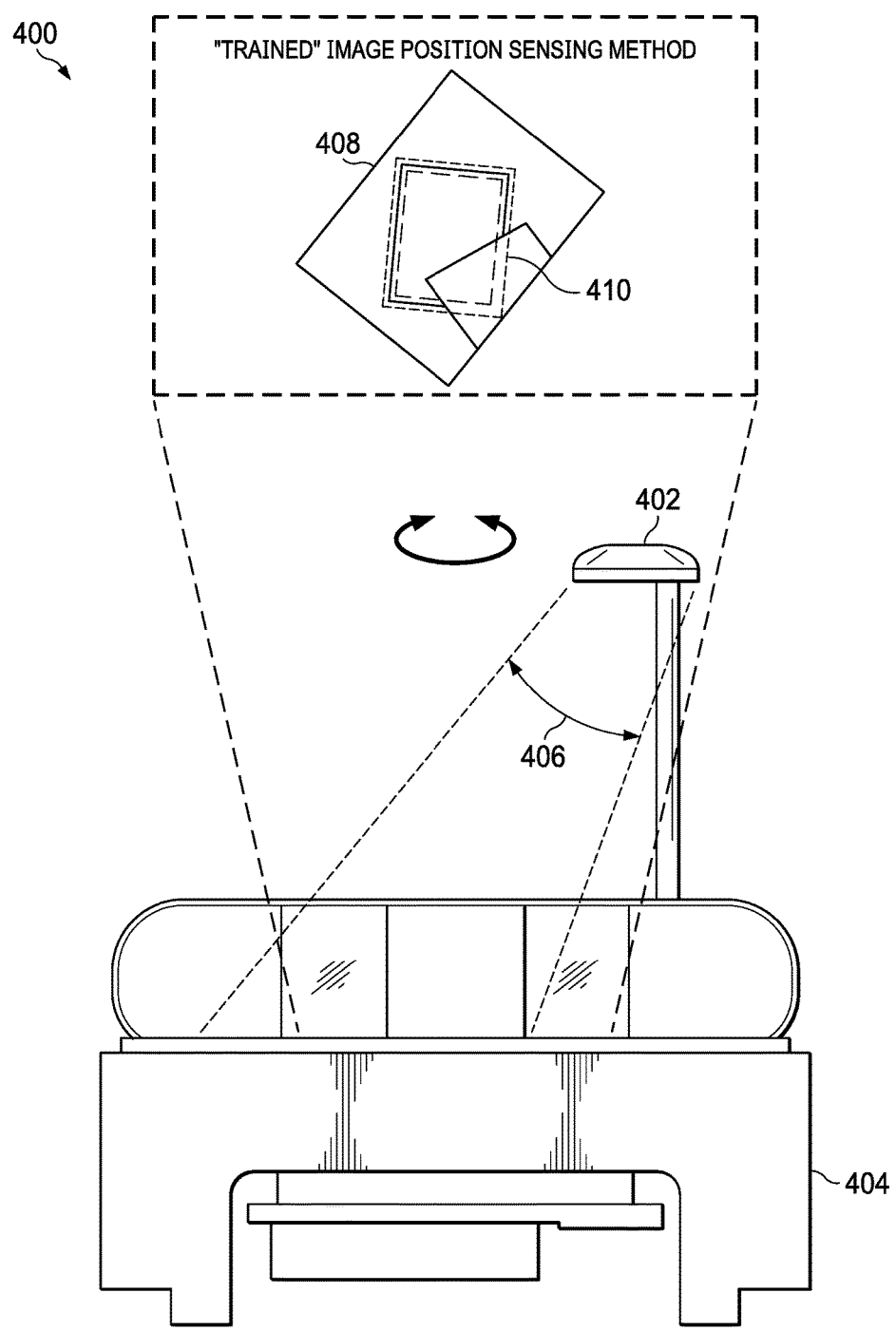
FIG. 4 is an illustration of an illustrative barcode reader system having a code reader configured to perform trained image position sensing to support orientation identification.

With regard to FIG. 4, an illustration of a barcode reader system 400 having a barcode reader 402 configured to perform scanning when in a "trained" image position to support orientation identification is shown. The barcode reader system 400 may include the barcode reader 402 and a base 404, as previously described with respect to FIG. 3. The barcode reader 402 may be configured to have a field-of-view 406 in which the barcode reader 402 may scan for items. The base 404 may include at least one template 408 that the barcode reader 402 has been trained to identify as corresponding with an orientation. The barcode reader 402 may include a guide template 410 that may assist in aligning with the template 408 as well as orientation detection.

In one embodiment, one or more orientations of a housing of the barcode reader 402 may include a respective template that the barcode reader 402 may be trained to identify. The different trained templates may include different configurations (e.g., markings, fixed features, such as scan window edges, stickers, or otherwise) so that the barcode reader 402 may identify a corresponding orientation based on the configuration of the trained template 408.

With regard to FIG. 5, an illustration of a barcode reader system 500 having a barcode reader 502 inclusive of an electromechanical sensor 504 formed of electrodes 506a-506n (collectively 506), positioned on a support stand 508, and used to determine orientation is shown. Rather than using electrodes, alternative sensing devices, such as optical sensors or otherwise, may be utilized to enable the barcode reader 502 to determine orientation of the reader 502. The electrodes 506 may provide voltage signal(s) that the barcode reader 502 may measure to determine angular orientation of the barcode reader 502. In an embodiment, as the barcode reader 502 is rotated, different signals may be read from a configuration of the electrodes 506. For example, the electrodes 506 may be configured such that when the different electrodes 506 are contacted by a set of complimentary electrodes in electrical communication with the barcode reader 502, a respective binary signal is communicated or sensed by the barcode reader 502.

In one embodiment, the electromechanical sensors 508 may be include a predetermined number of sensors configured so that varying angular orientations of the housing cause different electrodes or sensors to align so that the orientation signal may represent a configuration of the electrodes 506 and a corresponding orientation. The stand of the base 504 and the connecting mechanism may house a wire that electrically couples the barcode reader 502 to the base 504. In one embodiment, the wire may transmit a power source from the base 504 to the barcode reader 502. In one embodiment, the wire may also be configured to support data communications between the barcode reader 502 and the base 504.

Figure 6:
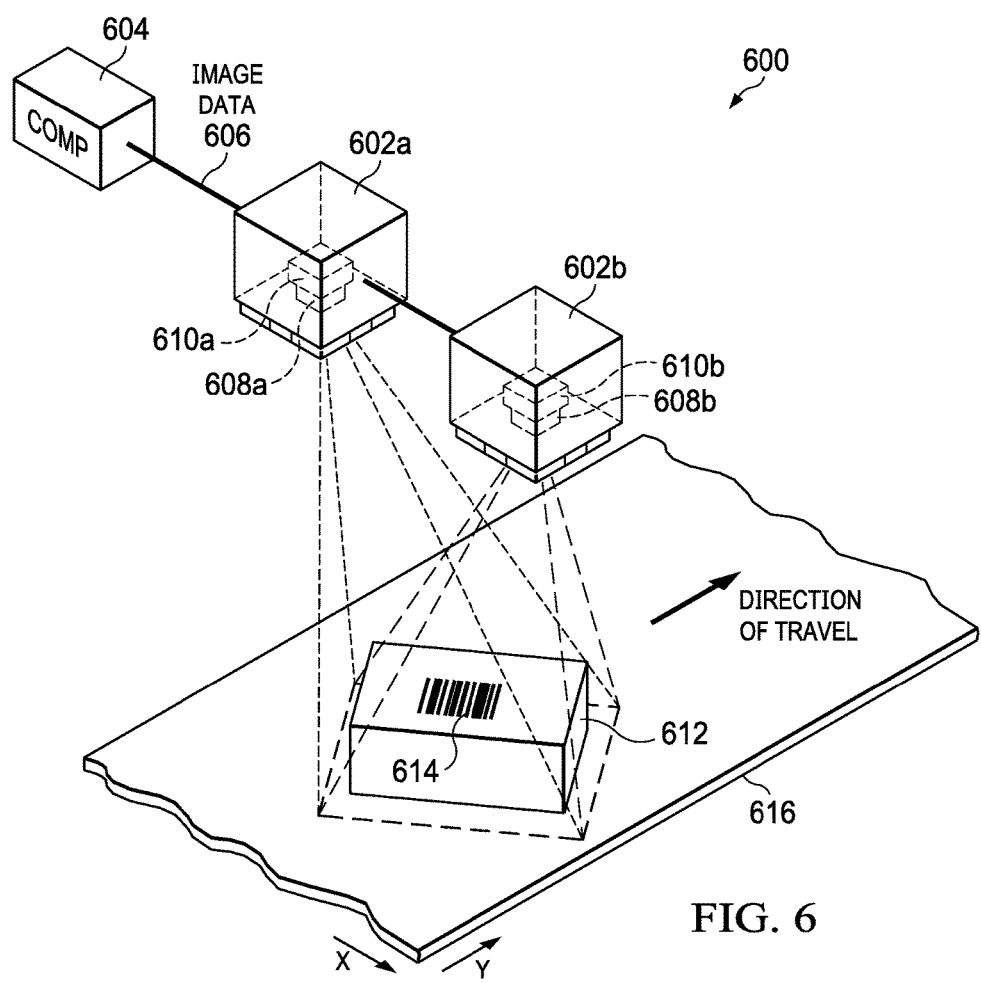
FIG. 6 is an illustration of an illustrative machine-readable indicia scanner for use in scanning machine-readable indicia, such as barcodes, QR codes, or other machine-readable indicia along with physical dimensions of products or packaging.

With regard to FIG. 6, an illustration of a machine-readable indicia scanner system 600 for use in scanning machine-readable indicia, such as barcodes, QR codes, or other machine-readable indicia along with physical dimensions of products or packaging is shown. The scanner system 600 may additionally and/or alternatively be configured to operate as a product inspection system or logistics processing system. The scanner system 600 may include cameras 602a and 602b (collectively 602) configured to capture images of an object 612, and generate image data 606 and/or data (e.g., codes) representative of the machine-readable indicia. The cameras 602 may include optics 608a and 608b (collectively 608), which may include lens(es), window, optical filter(s), and so on, and image sensors 610a and 610b (collectively 610) may be used for imaging a scene. In an embodiment, the image data 606 captured by the cameras 602 may be communicated to a computer system 604 for processing (e.g., reading a code from a machine-readable indicia) thereby. Alternatively, the cameras 602 may be configured with processing units (not shown) to process image data 606 and generate data derived therefrom (e.g., text representative of machine-readable indicia). In an embodiment, the cameras 602 and computer system 604 may be formed as single units. In one embodiment, the cameras 602 are configured (e.g., spatially aligned) so that the image data 606 from camera 602a and camera 602b may combine to produce a three dimensional image, as understood in the art. Although the scanner system 600 shows two cameras 602, a single camera or more than two cameras may be utilized to capture images from similar or different angles.

In an embodiment, the cameras 602 may identify markings, such as words, stickers, or features on a conveyer belt 616 that cause the cameras 602 to automatically enter a certain function or establish certain parameter(s).

As shown, an object 612 on which a machine-readable indicia 614 is positioned on the conveyer belt 616 that operates to move the object 612 along a direction of travel of the conveyer belt 616. When the cameras 602 image the object 612, the optics 608 and image sensors 610 may have some level of blur in the image, thereby being problematic for conventional image processing, as previously described. Depending on height of the object 612, speed of the conveyer belt 616, resolution of a machine-readable indicia 614 associated with, in this case attached to, the object 612, illumination of the indicia 614, optical noise, and so on may also contribute to difficulty in reading or decoding the indicia 614 by conventional image processing techniques. As a result, a processing unit of the computer system 608 may be configured to automatically utilize an algorithm that generates a virtual scanline in response to recognition of certain system parameters and machine-readable indicia type (acting as different "orientations" and corresponding "functions") to be able to more accurately determine or decode codewords of the machine-readable indicia.

Figure 7:
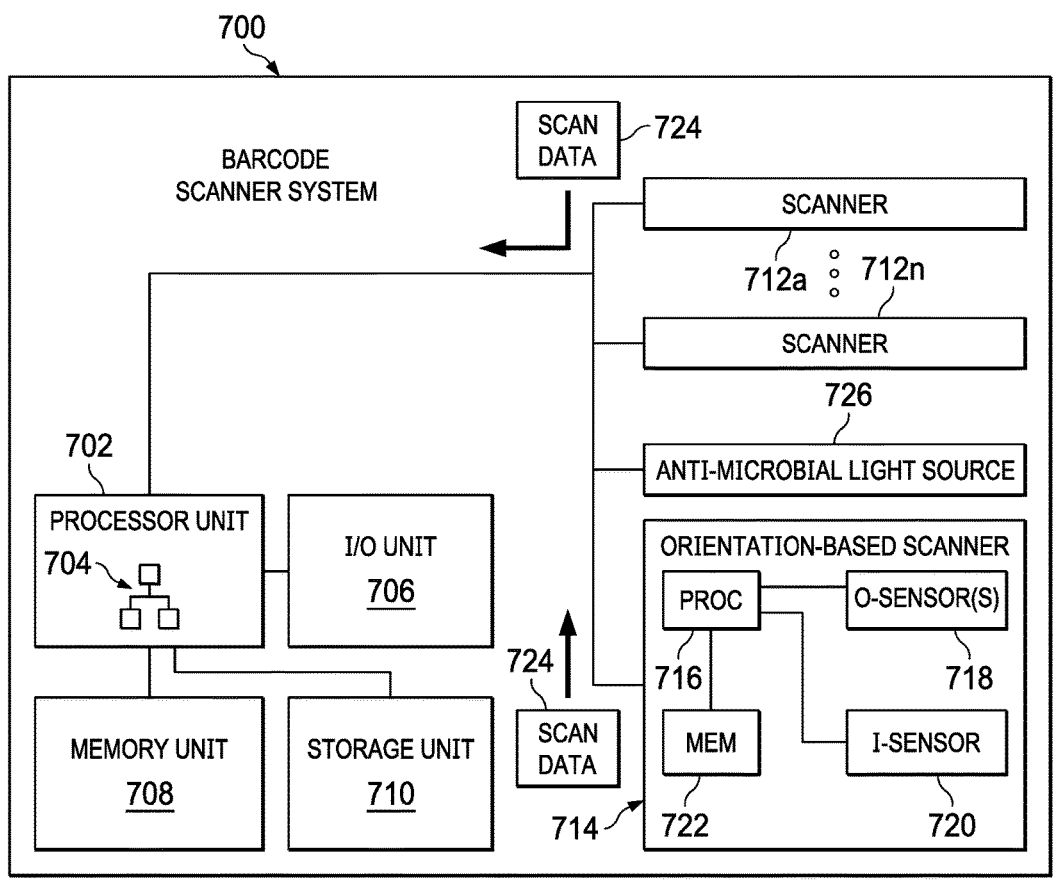
FIG. 7 is a block diagram of illustrative components of a code reader system that selects a function for a code reader based on an orientation thereof.

With regard to FIG. 7, a block diagram of components of a code reader system 700 that selects a function for a code reader based on an orientation thereof is shown. The code reader system 700 may include a processing unit 702, an input/output (I/O) unit 706 for communicating data, such as image data, a memory unit 708, a storage unit 710, scanners 712a-712n (collectively 712), and an orientation-based scanner 714.

The processing unit 702 may include a single processor or multiple processors. The processing unit 702 may further include suitable logic, circuitry, and interfaces that are operable to execute one or more instructions 704, such as, for example, modules 800 of FIG. 8, based on sensor and other data received to perform operations of a scanner. The processing unit 702 may be realized through a number of processor technologies known in the art. The examples of the processing unit 702 may include, but are not limited to, an x86 processor, an ARM processor, a Reduced Instruction Set Computing (RISC) processor, an Application-Specific Integrated Circuit (ASIC) processor, an image processor, a digital signal processor, or a Complex Instruction Set Computing (CISC) processor. The I/O unit 706 may be configured to communicate data over a communications network (e.g., the Internet, wireless communications network, and so on).

The orientation-based scanner 714 may be any of the code readers described herein with reference to FIGS. 1-6. The orientation-based scanner 714 may include a processing unit 716, one or more orientation sensors 718, an image sensor 720, and memory 722. The scanners 712 and orientation-based scanner 714 may communicate scan data 724 to the processing unit 702. The scan data 724 may include data corresponding with an orientation of a housing of the orientation-based scanner 714. The scan data 724 may include image data, code represented by a machine-readable indicia, or other data format that may be used or combined with other data by another processor operating on a host system (e.g., POS system), for example, based on a function in which the orientation-based scanner 714 is operating. It should be understood that the use of the housing as an orientation reference is arbitrary, and that any other object, such as a portion of a stand on which a barcode scanner is positioned, may be considered relative to the housing.

The orientations sensor(s) 718 may be any sensor that is capable of measuring angular or other position of the orientation-based scanner 710. The image sensor 720 may include an optical camera and processing unit or otherwise (i) that enables a visual orientation of the orientation-based scanner 710 to be used in determining orientation as well as (ii) captures images to perform reading of machine-readable indicia or otherwise.

The code reader system 700 may also include an anti-microbial light source 726. In one embodiment, the anti-microbial light source 726 may include a light emitting diode (LED) configured to emit an illumination having a wavelength between approximately 380 nanometers and approximately 470 nanometers, which are blue wavelengths. In an embodiment, the anti-microbial light source 726 may additionally and/or alternatively include an ultraviolet lighting elements (e.g., LEDs). It should be understood, however, that it has been found that ultraviolet light may be harmful to humans, so the use of ultraviolet light may be limited to times during which no humans are determined to be present through sensing (e.g., motion sensing, light sensing, notification from local security system, etc.), timing (e.g., between 1 AM and 5 AM), covering (e.g., shade pulled over workstation), or other means. The anti-microbial light source 726 may be used to clean or disinfect surfaces from unwanted microbes (i.e., deactivate or kill germs and/or bacteria). The anti-microbial light source 726 may be used to clean or disinfect the surfaces, which may include a workspace, touch points on a scanner and/or point-of-sale, etc., without cleaning chemicals that are often harmful to and/or degrade materials, such as polycarbonate and ABS, that are often used on data collection workspaces, on point-of-sale counters, on barcode scanners, or elsewhere in commercial settings at which barcode scanners are used.

Figure 8:
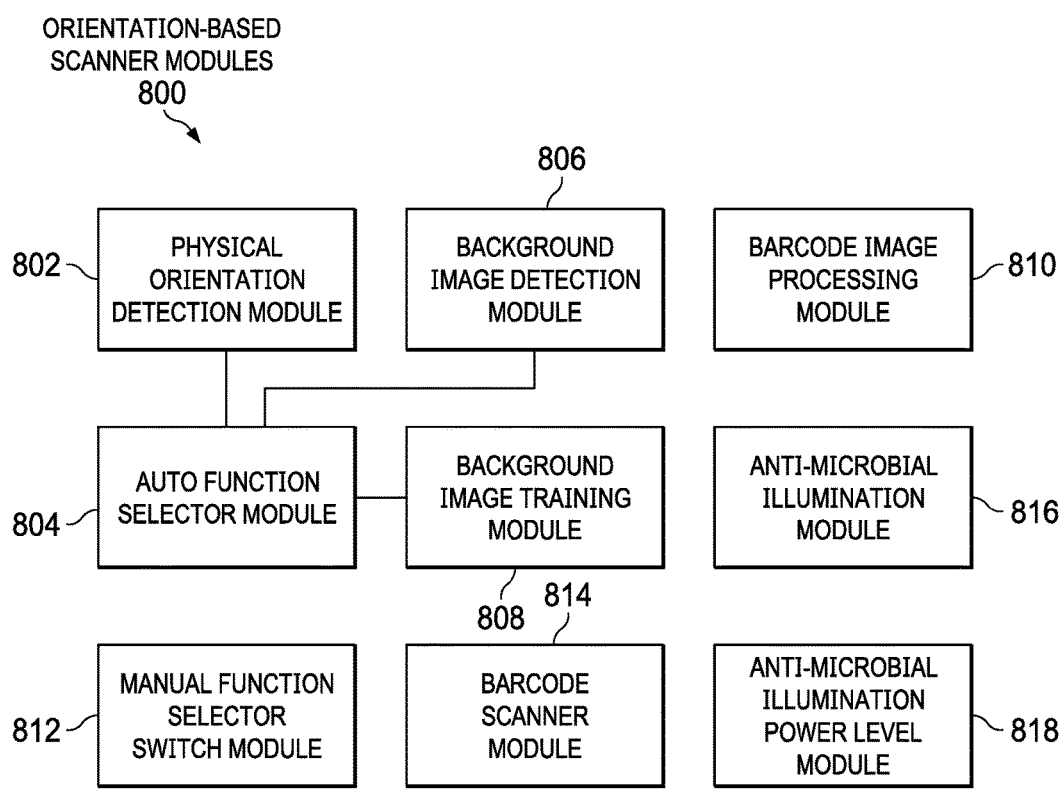
FIG. 8 is a block diagram of illustrative modules performed by a code reader system configured to automatically select functions based on orientation and perform barcode reading using a selected function.

With regard to FIG. 8, a block diagram of modules 800 executed by a barcode reader system or barcode reader configured to automatically select and perform functions based on orientation and perform barcode reading using a selected function is shown. The modules 800 may include modules for detecting orientation and selecting a corresponding function, such as, but not limited to, a physical orientation detection module 802, an automatic function selector module 804, a background image detection module 806, and a background image training module 808. The physical orientation detection module 802 may include detecting an orientation and/or a change in orientation. The automatic function selector module 804 may be configured to select a function corresponding with an orientation detected by the physical orientation detection module 802.

In an embodiment, the number of available functions may be five, as described with regard to FIGS. 2 and 3. Other numbers of functions are also possible.

The background image detection module 806 may be configured to detect a background according to any of the hereinabove described background detection methods. The background image detection module 806 may be configured to search for and detect predetermined parameters of a background image obtained by an image sensor. The background image training module 808 may include capturing an image of a background when the barcode reader is in an orientation, and processing an indicator of a portion, or all, of an image captured by an image sensor. The image captured or derivation thereof may be stored in memory and a corresponding orientation may be assigned thereto. The background image training module 808 may include identifying parameters of a background image obtained by the image sensor that may be easily detected in subsequent scans of objects with the same background. For example, a rectangle in which checks are scanned may be used to define a recognizable pattern that is within a background portion of an image when the scanner is rotated or otherwise positioned to capture an image inclusive of the rectangle, thereby informing the module 804 of the barcode reader to change to a check reader function. Additionally and/or alternatively colors, shapes, or other visually distinguishing features on a surface that defines a background portion of an image of a target area in which objects may be scanned may be utilized to determine orientation via image training and image processing.

The modules 800 may also include a barcode image processing module 810, a manual function selector switch module 812, and a barcode scanner module 814. In one embodiment, the manual function selector switch module 812 receives a communication, such as a signal from a switch or user interface, from a user in order to direct the processing to select a function identified in the user communication. The barcode scanner module 814 may include scanning a machine-readable indicia on an item in a field-of-view of a code reader inclusive of the modules 800. The barcode scanner module 814 may further include capturing an image of a machine-readable indicia, or barcode, disposed on the item. The machine-readable-indicia may be a code representative of the item. The barcode image processing module 810 may include (i) receiving an image of a machine-readable indicia from the barcode scanner module 814 and (ii) processing the image to determine the code of the machine-readable indicia representative of the item.

The modules 800 may also include an anti-microbial illumination module 816 and an anti-microbial illumination power level module 818. The anti-microbial illumination module 816 may be configured to initiate an emission of an anti-microbial illumination by the barcode scanner with anti-microbial illumination devices in response to the code reader being in an orientation corresponding with a cleaning function. The module 816 may additionally and/or alternatively be configured to initiate an emission of an anti-microbial illumination in response to other triggers or inputs, including a periodic (e.g., timer) or aperiodic (e.g., activation of a manual switch) event. In one embodiment, the anti-microbial illumination module 816 may receive an input that the code reader is in the orientation corresponding with the cleaning function. The anti-microbial illumination module 816 may be configured to stop an emission of the anti-microbial illumination in response to receiving an input that the code reader is configured in a non-anti-microbial illumination orientation. In one embodiment, the anti-microbial illumination module 816 may cause the anti-microbial illumination to be emitted by anti-microbial illumination device(s) when the code reader is powered on. In one embodiment, the anti-microbial illumination module 816 may cause the anti-microbial illumination to be emitted by the code reader after a single use or multiple uses of the code reader. In one embodiment, the anti-microbial illumination module 816 may cause the anti-microbial illumination to be emitted when a venue of the code reader is closed and/or unoccupied based on a timer, ambient lighting, audio sensing, motion sensing, and/or otherwise. It should be understood that the module 816 may be configured to turn on and off the anti-microbial illumination device(s) using a variety of other inputs that the module 816 uses to determine when to turn on and off the anti-microbial illumination device(s).

The anti-microbial illumination power level module 818 may be configured to control a power level of the anti-microbial illumination by anti-microbial illumination device(s). As an example, module 818 may be configured to cause the code reader to emit the anti-microbial illumination at a first power level when the code reader is in an orientation corresponding with a scanning function. The module 818 may further be configured to cause the code reader to emit the anti-microbial illumination at a second power level, which may be greater than the first power level, when the code reader is in an orientation corresponding with a cleaning or disinfection function.

The anti-microbial illumination power level module 818 may cause the anti-microbial illumination be emitted at either the first power level or the second power level in response to the code reader being in a corresponding orientation. For example, the code reader may be in a reading orientation, which may cause the module 816 to maintain the anti-microbial illumination device(s) to be off, in which case the module 818 does not set a power level of the anti-microbial illumination device(s), or be on and send an input (e.g., reader in reading mode) to the module 818 that drives the anti-microbial illumination device(s) to be in a first (low) illumination level. In an alternative embodiment, the module 818 may be configured to set an illumination level in response to periodic and/or aperiodic events described hereinabove with regard to the anti-microbial illumination module 816. It should be understood that the module 818 may be configured to set power level of the anti-microbial illumination device(s) based on a variety of different rules or conditions. A retractable diffuser may be disposed in front of the anti-microbial illumination device(s) to distribute sanitizing light.

With regard to FIG. 9, a flow diagram of a method 900 of automatically selecting a function of a code reader based on an orientation thereof is shown. The method 900 may include a step 902 of sensing a new orientation of a housing of the code reader. In sensing the new orientation, any of the hereinabove referenced sensing methods, such as, for example, sensing a new orientation of a housing of a code reader by an electromechanical sensor may be used.

The method 900 may then automatically change a function of the code reader based on the new orientation at step 904. A processing unit of the code reader may access a database or table in a memory of corresponding functions and orientations. Based on the new orientation, the processing unit may select the corresponding function as listed in the database. In one embodiment, the processing unit may receive an orientation signal indicating that a new orientation has been sensed. The processing unit may respond to the orientation signal to identify the new orientation. In another embodiment, the new orientation may be identified in the orientation signal. For example, if a set of electrical contacts define different positions of the barcode reader, then the processing unit may switch a function corresponding to the identified orientation (e.g., 1=barcode scanning, 2=check scanning, etc.). At step 906, the processing unit may update a portion of memory with the new orientation.

With regard to FIG. 10, a flow diagram of a method 1000 of automatically selecting a function of a code reader based on an orientation thereof is shown. The method 1000 may begin with step 1002 when a scan is initiated. In one embodiment, the scan is initiated in response to a user communicating to a processing unit of a code reader to initiate a scan, such as, for example, squeezing a button or trigger on the code reader to initiate the scan. In another embodiment, the scan may be automatically initiated by identifying an item entering into a target area. The scan may be automatically initiated and the item sensed by at least one of electronics internal to the code reader and electronics external to the code reader.

At step 1004, an orientation of the housing may be detected. In one embodiment, the code reader may include a sensor for sensing orientation of the housing. In another embodiment, the orientation may be detected by an image of a background of the target area. One of skill in the art will appreciate that many methods exist for detecting orientation, such as, but not limited, the methods of detecting orientation as described herein. At step 1006, the processing unit may determine if the detected orientation is different than a current orientation as stored in memory. If the orientations are different, the processing unit may change a function of the code reader based on the detected orientation at step 1008. In one embodiment, the processing unit may update the current orientation in memory with the detected orientation. At step 1010, the code reader may scan the target area using a function corresponding to the detected orientation. The processing unit may direct components of the code reader to perform scanning functions corresponding with the detected orientation at step 1012. The functions may be functions described hereinabove with reference to FIGS. 1-6. The difference between the processes 900 and 1000 is the trigger as to when a function of the barcode reader is changed.

Figure 11B:
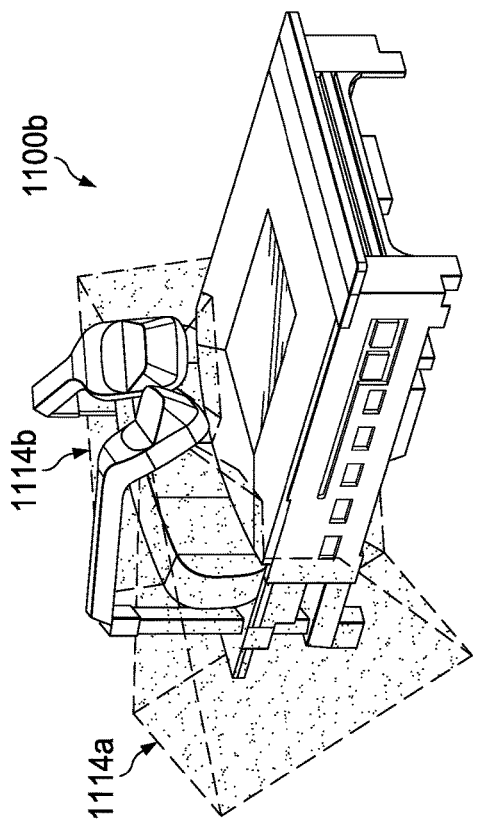
FIGS. 11A and 11B are illustrations of illustrative code readers in orientations corresponding with a cleaning function.
Figure 11A:
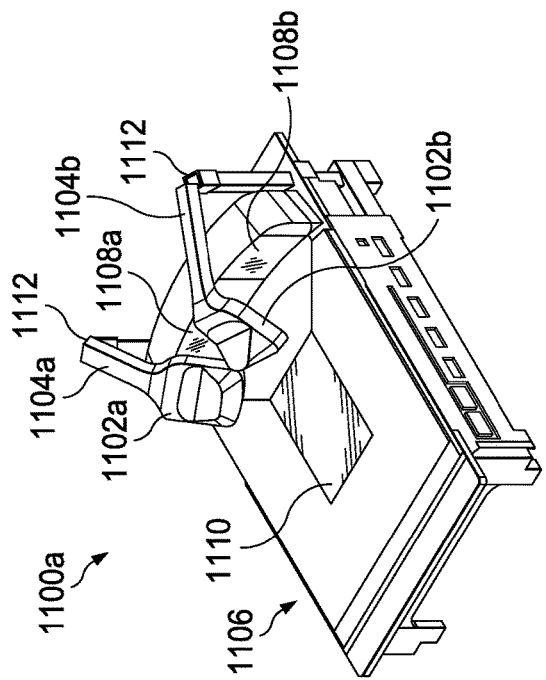

With regard to FIGS. 11A and 11B, illustrations of illustrative code readers 1100a and 1100b (collectively 1100) positioned in an orientations corresponding with a cleaning function are shown. The code readers 1100 may include a first scanner 1102a and a second scanner 1102b (collectively 1102) that are positioned on arms 1104a and 1104b (collectively 1104) to enable the scanners 1102 to read machine-readable indicia on objects positioned. In addition to the scanners 1102, the code reader 1100 may also include side-view scanners 1108a and 1108b (collectively 1108) that are oriented to read machine-readable indicia positioned on objects when facing the scanner(s) 1108. A bottom scanner 1110 may be positioned beneath the surface 1106 to scan machine-readable indicia facing downwards on the objects placed on the surface 1106.

To initiate a disinfecting or cleaning function, the scanner(s) 1102 may be positioned in an orientation corresponding with the cleaning function by rotating the arm(s) 1104 at joints 1112a and 1112b along the respective arms 1104. The cleaning function may be executed by turning on anti-microbial illumination devices (not shown) that illuminate fields-of-view 1114a and 1114b (collectively 1114) of the scanners 1102. The disinfecting function may disinfect surfaces within the fields-of-view 1114 of the scanner(s) 1102 that may include, but are not limited to, the surface 1106, objects being scanned, user interface (e.g., keyboard), a housing of the scanner(s) 1102, and/or any other surface or object in the fields-of-view 1114. In one embodiment, the housing of the scanners 1102 may be substantially transparent so that the emitted anti-microbial illumination may clean the housing.

In one embodiment, the scanner(s) 1108 may also be configured with anti-microbial illumination device(s) to disinfect the surface 1106 and/or anything in fields-of-view of the scanners 1108. The third scanner 1110 may also be configured with anti-microbial illumination device(s) to disinfect the surface 1106 and/or anything in the field-of-view of the scanner 1110. One of skill in the art will appreciate that a number of combinations of anti-microbial illumination may be incorporated into the scanners 1102, 1108, and 1110 or elsewhere at the code reader 1100.

Figure 12B:
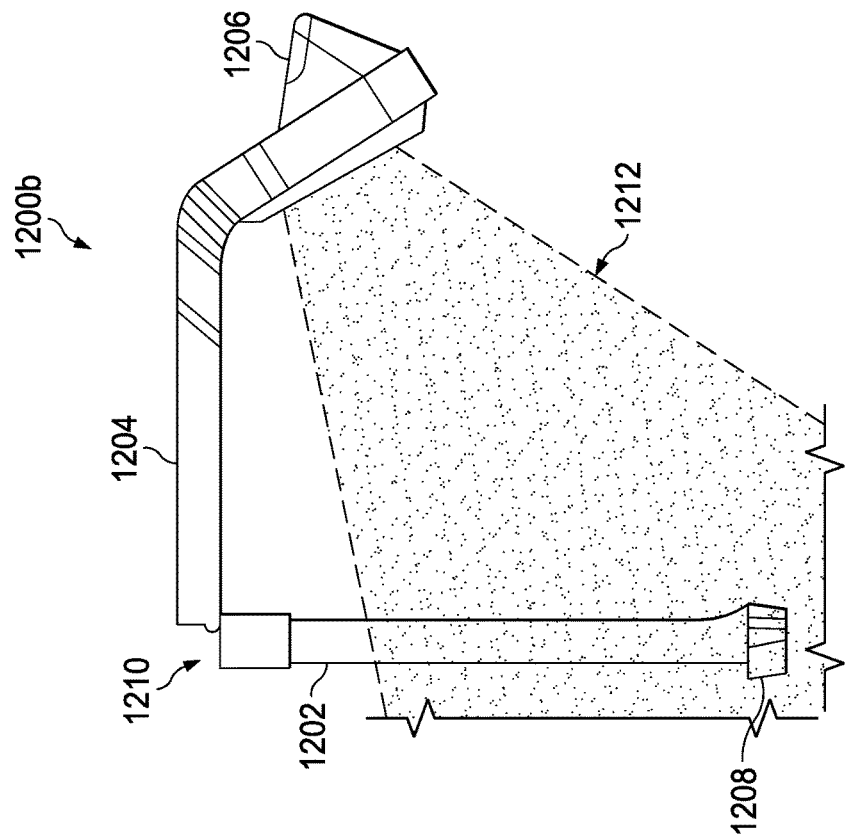
FIGS. 12A and 12B are illustrations of an illustrative top-down reader inclusive of a light source configured to emit an anti-microbial illumination for cleaning.
Figure 12A:
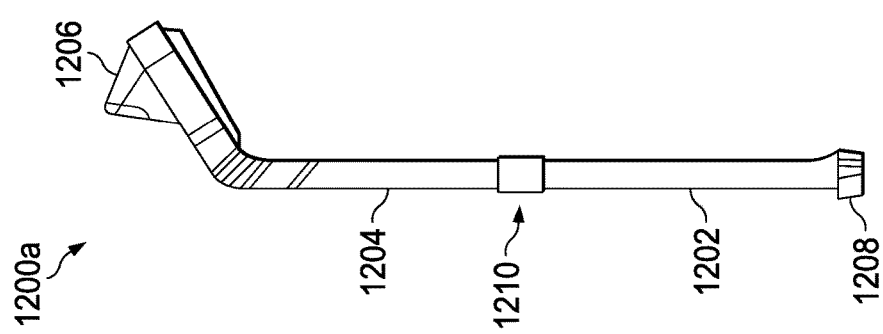

With regard to FIGS. 12A and 12B, illustrations of an illustrative top-down reader 1200a, 1200b (collectively 1200) inclusive of an anti-microbial illumination source configured to emit an anti-microbial illumination for cleaning or disinfecting are shown. The top-down reader 1200 may include a lower portion 1202, an upper portion 1204, and a scanner 1206.

The top-down reader 1200 may be configured to extend upward from a housing of a code reader, such as the code reader 1100a of FIG. 11A, via an adapter 1208 that may be rotatable or otherwise enable a user to rotate the scanner 1206 relative to the code reader. In an embodiment, a joint 1210 between the upper portion 1204 and lower portion 1202 may be configured to enable the upper portion 1202 and lower portion 1204 to be axially rotatable relative to one another. In addition and/or alternatively, the joint 1210 may enable the upper portion to be rotated downwards toward the bottom portion 1202. In one embodiment, sensors (not shown) may be disposed within or at the joint 1210, such as the electromechanical sensors 508 of FIG. 5, to sense axial rotation of the upper portion 1202 relative to the lower portion 1204. Other sensor(s) (not shown) may be configured to detect vertical rotation of the upper portion 1202 relative to the lower portion 1204. In an embodiment, the top-down reader 1200 may be configured to have at least two orientations that may include an upright orientation, such as the top-down reader 1200a of FIG. 12A, and a non-upright orientation, such as the top-down reader 1200b of FIG. 12B.

In one embodiment, the non-upright orientation of the top-down reader 1200b may correspond with a cleaning function. The cleaning function may include the scanner 1206b emitting an anti-microbial illumination into a field-of-view 1212 of the scanner 1206b. In one embodiment, the top-down reader 1200 may be configured with a sensing device, such as a mercury switch, gyroscopes, accelerometers, or otherwise, to sense that the top-down reader 1200 is in an orientation corresponding with the cleaning function, and respond by executing the cleaning function (e.g., turning on anti-microbial illumination devices, and possibly at one of multiple possible illumination intensity levels). In one embodiment, a processing unit or static logic of the code reader 1200 may sense that the top-down reader 1200 is in the orientation corresponding with the cleaning function and respond by communicating a command to execute the cleaning function to the top-down reader 1200.

With regard to FIGS. 13A-13C, illustrations of an illustrative code reader 1300 inclusive of scanners 1302a and 1302b (collectively 1302) and a reflective roller shade 1304 for use during a cleaning function are shown. The reflective roller shade 1304 may be configured to cover the scanners 1302 to create a covered workspace 1306. The covered workspace 1306 may be substantially dark and provide a more efficient disinfecting condition for the cleaning function to kill germs and bacteria. In one embodiment, the code reader 1300 may include a sensor (see FIG. 14A) for sensing when the covered workspace is dark and in a condition for the cleaning function.

More specifically, the cleaning function may include the scanners 1302 emitting an anti-microbial illumination into the covered workspace 1306. The anti-microbial illumination may reflect off of the reflective roller shade 1304 and clean additional portions of the code reader external to a field-of-view of the scanners 1302.

In one embodiment, the code reader 1300 may include additional scanners 1308*a* and 1308*b* (collectively 1308) that may also be configured to emit an additional anti-microbial illumination to the anti-microbial illumination emitted by the scanners 1302. In one embodiment, the reflective roller shade 1304 may be configured to be retractable for ease of use by a user of the code reader 1300. The roller shade 1304 may be manually positioned and retracted. In another embodiment, an event, such as a "clean" setting being selected via a user interface, may trigger (e.g., electronic command signal) the reflective roller shade 1304 to automatically deploy over the code reader 1300.

Figure 14B:
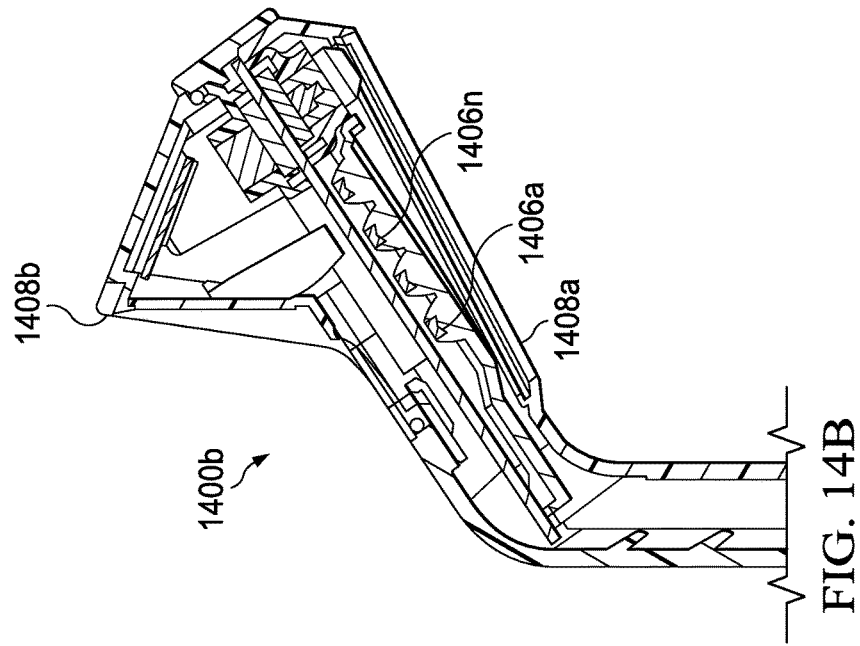
FIGS. 14A and 14B are illustrations of an illustrative scanner inclusive of an image sensor and a light source configured to be used in cleaning functions and scanning functions.
Figure 14A:
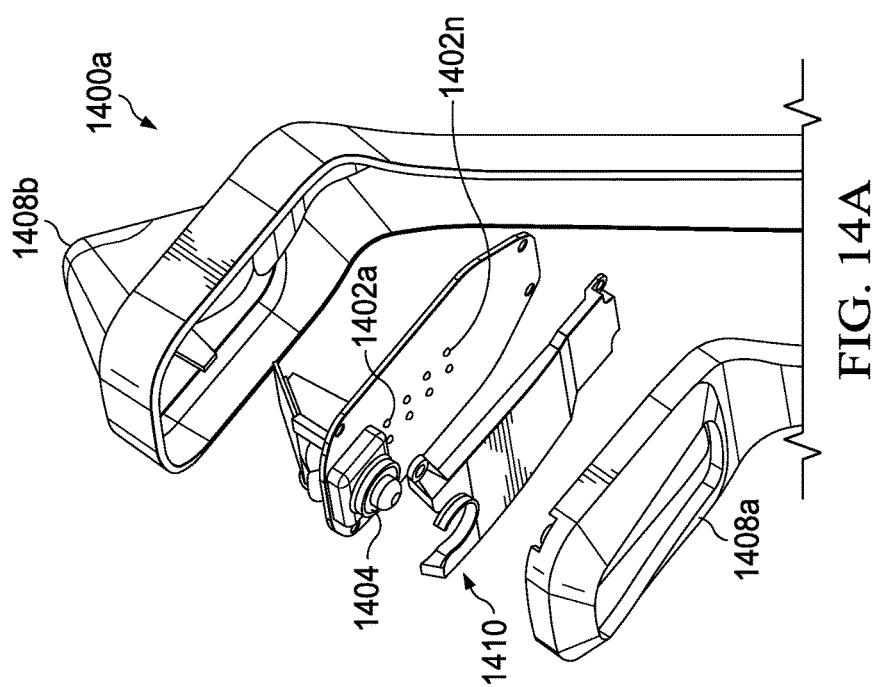

With regard to FIGS. 14A and 14B, illustrations of an illustrative scanner 1400*a*, 1400*b* (collectively 1400) inclusive of light sources 1402*a*-1402*n* (collectively 1402), and an image sensor 1404 configured to be used in cleaning functions and/or scanning functions are shown. The scanner 1400 may also include illumination lenses 1406*a*-1406*n* (collectively 1406) and housing members 1408*a* and 1408*b* (collectively 1408). The scanner 1400 may be a scanner of a code reader, such as the scanners 1102, 1206, and 1302 of FIGS. 11A-13C.

The light sources 1402, image sensor 1404, and illumination lens 1406 may be disposed within the housing 1408. The housing 1408 may include a lower portion 1408*a* and an upper portion 1408*b* that attach to one another. In one embodiment, the light sources 1402 and image sensor 1404 may be coupled to a cover 1410 for physical protection.

The light sources 1402 may include eight multi-color LEDs that correspond with eight illumination lenses 1406 to direct and shape an illumination field-of-view. The light source 1402 may be configured to emit a plurality of combinations of colors in response to different orientations of the code reader. In one embodiment of the code reader being in an orientation corresponding with a scanning function, the light source 1402 may emit (i) a red illumination only for performing reading of a machine-readable indicia, (ii) a combination of blue illumination and red illumination for disinfecting/reading, or (iii) any other combination of colors including or not including the blue illumination. The blue illumination may be an anti-microbial wavelength and/or ultraviolet wavelength. In one embodiment of the code reader being in an orientation corresponding with a cleaning function, the light source 1402 may emit only a blue illumination. Other colors during the cleaning function may be utilized, even for decorative purposes, so long as the anti-microbial functionality of killing harmful bacteria is not reduced. A power level of the anti-microbial illumination may be fixed, have multiple power levels, or be variable (e.g., change wavelengths and/or power levels over time). The power level may be set based on a setting or may be set by a manufacturer. As previously described, the level of the anti-microbial illumination may be set depending on a configuration, such as a cover being positioned for a cleaning mode, scanner with the anti-microbial light sources being placed into a particular position, setting be selected, or otherwise, of the code reader. If the barcode reader uses an image sensor, then the reader may be configured with anti-microbial illumination device(s) and, optionally, guide lights to assist a user with positioning a machine-readable indicia for scanning.

Figure 15:
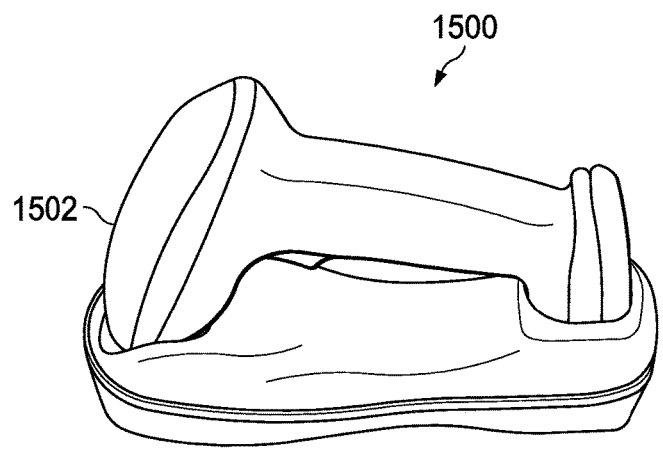
FIG. 15 is an illustration of an illustrative handheld code reader having a substantially transparent housing.

With regard to FIG. 15, an illustration of an illustrative handheld code reader 1500 having a substantially transparent housing 1502 is shown. The handheld code reader 1500 may include a light source disposed within the housing 1502 and configured to emit an anti-microbial illumination over blue wavelengths, as previously described. In one embodiment, the light source may also be configured to scan an object. In one embodiment, the light source may be configured to emit the anti-microbial illumination outward to a portion of the housing 1502 that is held by a user and may be additional to a light source for scanning objects. One of skill in the art will appreciate that a plurality of combinations of light sources, including, but not limited to, one light source and two or more light sources, may be used for scanning, cleaning, and disinfecting. It should be understood that other, non-handheld code readers may include a portion or entire translucent or transparent housing to enable disinfecting the code readers in addition to surfaces, such as workspaces on which food and items are placed during purchasing or processing (e.g., performing inventory) operations.

Figure 16:
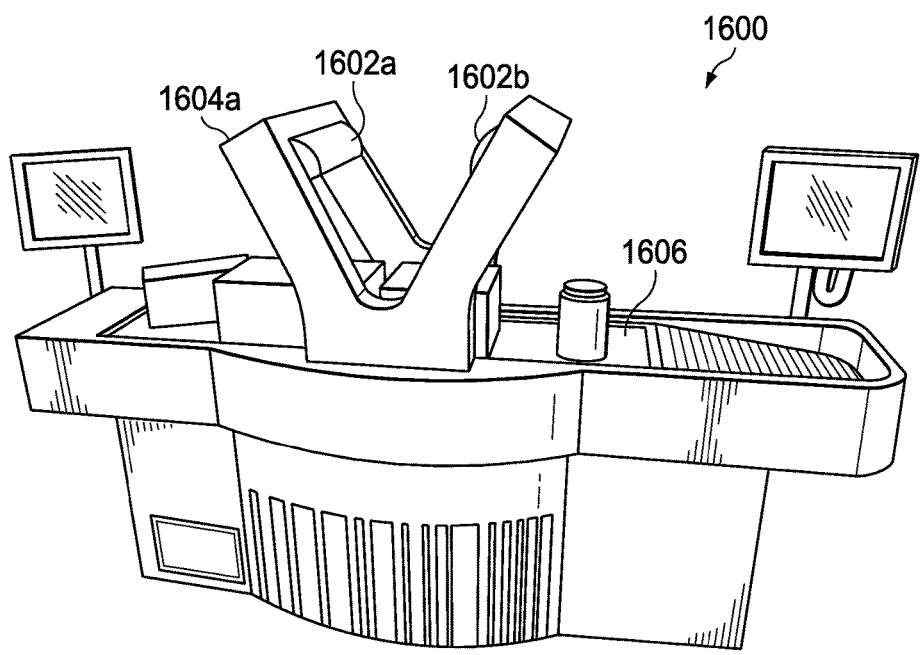
FIG. 16 is an illustration of an illustrative code reader inclusive of a conveyor belt with overhead scanner and having a cleaning function.

With regard to FIG. 16, an illustration of an illustrative code reader 1600 inclusive of a conveyor belt 1604 with overhead scanners 1602*a* and 1602*b* (collectively 1602) positioned on arches 1604*a* and 1604*b* (collectively 1604) having a cleaning function is shown. In one embodiment, the overhead scanner 1602 may include a single arch including at least one scanner. In addition to the overhead scanners 1602 positioned on the arches, additional scanners may be positioned prior to, after, and beneath the arches 1604. The overhead scanners 1602, as well as any of the other scanners, may be configured with anti-microbial illumination sources to emit an anti-microbial illumination for cleaning and/or disinfecting the conveyor belt 1606. Additionally and/or alternatively, anti-microbial illumination devices may be positioned separate from the scanner and disposed inside of or external from the arches In one embodiment, the overhead scanners 1602 and any other scanner that may be configured with anti-microbial illumination source(s) may be configured to clean and/or disinfect the conveyor belt 1606 and/or other work surfaces in response to any number of triggers, as previously described. For example, the overhead scanner 1602 may be configured to perform a cleaning and/or disinfecting function at a regular time interval (e.g., at 3 AM) and for a predetermined duration (e.g., 30 minutes). The overhead scanner 1602 may also be configured to perform the cleaning and/or disinfecting function in response to a command from a user. The command from the user may be active (i.e., flipping a switch or pushing a button) or passive (i.e., shutting down the code reader 1600, performing an action or repositioning a component of the code reader 1600 to indicate that the code reader 1600 is done being used for a period of time).

In one embodiment, the overhead scanner 1602 may be configured to perform the cleaning and/or disinfecting function for a set length of time. The overhead scanner 1602 may be configured to perform the cleaning and/or disinfecting function for a set number of rotations of the conveyor belt 1606, such as 20 rotations). In operation, the conveyor belt 1606 may be controllable by a processing unit of the scanning system (e.g., a processing unit that is communication with each of the scanners at the code reader 1600) to turn on and off the conveyor belt 1606 during times that the cleaning function is being performed and controlling speed of the conveyor belt 1606 (e.g., slower than normal speed during a cleaning mode to enable higher durations of time of being exposed to the anti-microbial illumination). One of skill in the art will appreciate that many methods of initiating and timing a cleaning function may exist for operating the overhead scanner 1602.

Figure 17:
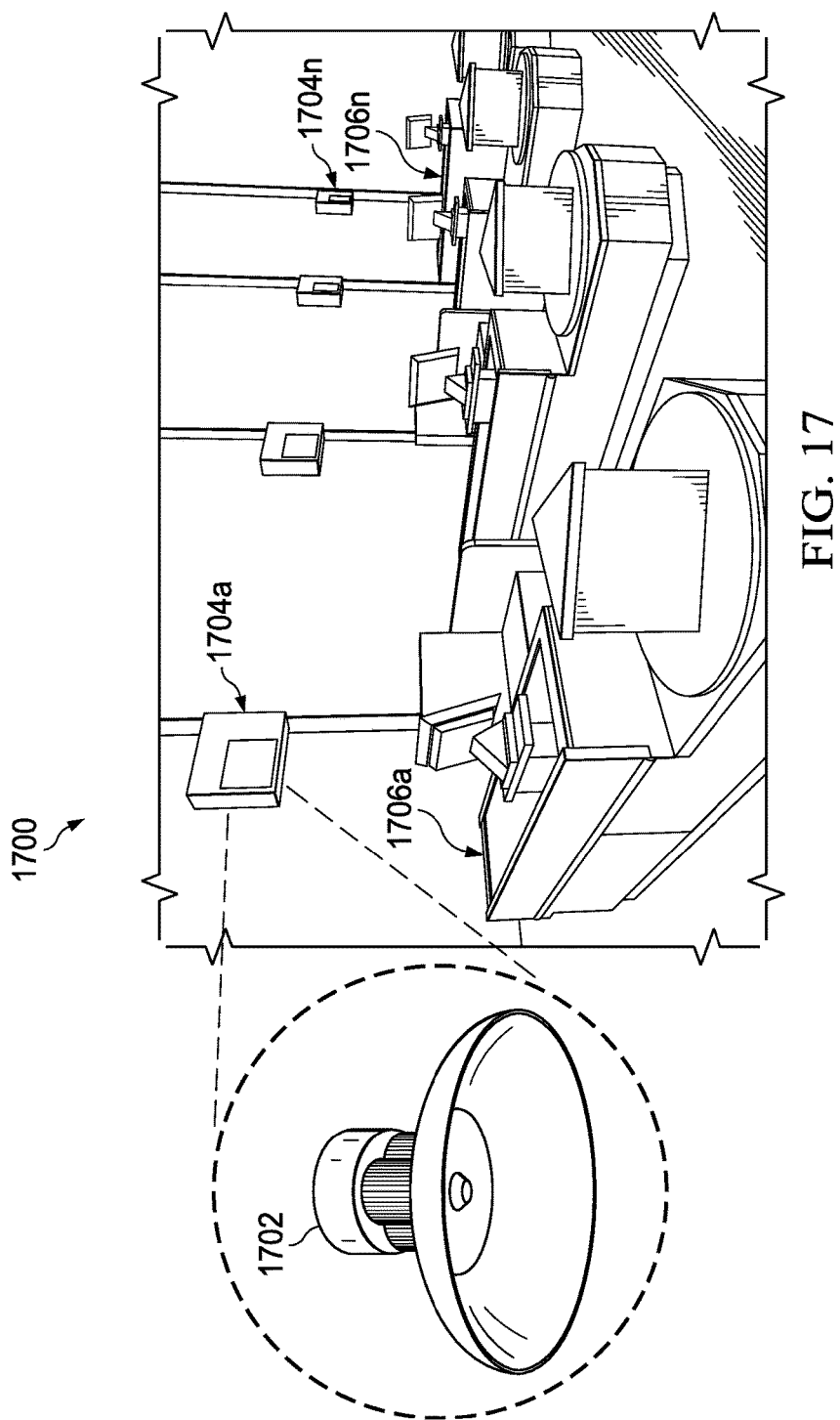
FIG. 17 is an illustration of an illustrative code reader station with an overhead anti-microbial illumination source for disinfecting a workspace of the station.

With regard to FIG. 17, an illustration of an illustrative code reader station 1700 with an overhead anti-microbial illumination source 1702 for disinfecting a workspace of the station is shown. The code reader station 1700 may include the overhead anti-microbial illumination source 1702 disposed in a housings 1704a-1704n (collectively 1704) that is configured to hang or are supported by a post above workstations 1706a-1706n (collectively 1706) such that the overhead anti-microbial illumination source 1702 may flood the workstation 1706 with anti-microbial illumination.

In one embodiment, the overhead anti-microbial illumination source 1702 may emit an anti-microbial illumination. The overhead anti-microbial illumination source 1702 may be configured to emit the anti-microbial illumination in response to at least one of actions, orientations, and other commands as described hereinabove with regard to FIGS. 11A-16. For example, the anti-microbial illumination source 1702 may be turned on in response to a scanner arm or other feature of the scanner being placed into a clean orientation. Other triggers may be utilized and illumination intensity may be set based on a variety of possible mechanisms, including motion sensing, light sensing, time of day, or any other sensing mechanism that enables a determination that no one is in a field-of-view of the anti-microbial illumination source 1702. The motion, light, and other sensing may be considered sensing environmental factors. In an embodiment, a first sense value (e.g., motion sensed, bright light sensed, etc.) that indicates that people may be local to the code reader may be used by a processor to maintain the anti-microbial illumination source 1702 at a first level, such as off or at a low power level, and a second sense value (e.g., no motion, darkness or low light sensed, etc.) that indicates that no one is local to the code reader may be used by the processor to turn on or increase the power level of the anti-microbial illumination source 1702.

Figure 18:
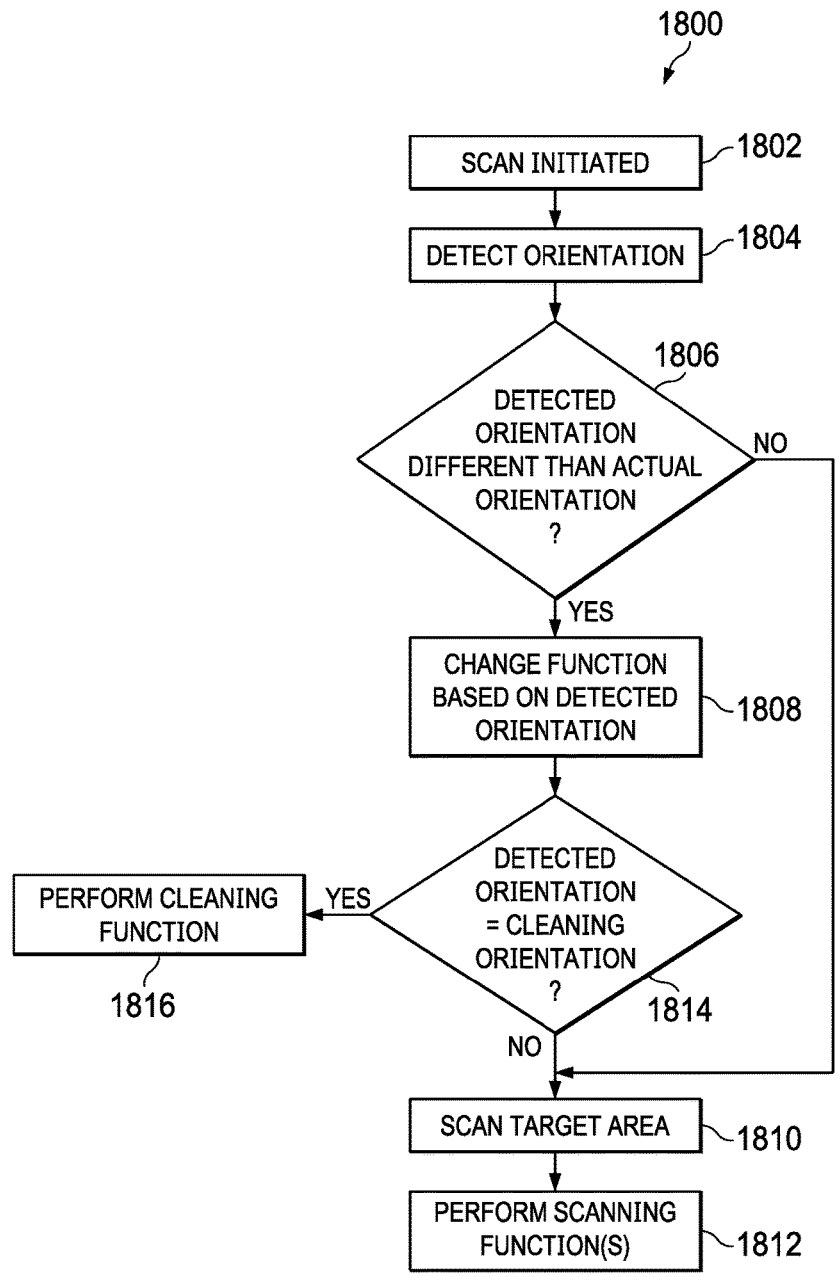
FIG. 18 is a flow diagram of an illustrative method of automatically selecting a function of a code reader based on an orientation thereof.

With regard to FIG. 18, a flow diagram of an illustrative method 1800 of automatically selecting a function of a code reader based on an orientation thereof is shown. The method 1800 may begin with step 1802 when a scan is initiated in the same or similar manner as FIG. 10. In one embodiment, the scan is initiated in response to a user communicating to a processing unit of a code reader to initiate a scan, such as, for example, squeezing a button or trigger on the code reader to initiate the scan. In another embodiment, the scan may be automatically initiated by identifying an item entering into a target area. The scan may be automatically initiated and the item sensed by at least one of electronics internal to the code reader and electronics external to the code reader.

At step 1804, an orientation of the housing may be detected. In one embodiment, the code reader may include a sensor for sensing orientation of the housing. In another embodiment, the orientation may be detected by an image of a background of the target area. One of skill in the art will appreciate that many methods exist for detecting orientation, such as, but not limited, the methods of detecting orientation as described herein. At step 1806, the processing unit may determine if the detected orientation is different than a current orientation as stored in memory. If the orientations are different, the processing unit may change a function of the code reader based on the detected orientation at step 1808. In determining orientations, the orientation may include physical position of a scanner with anti-microbial device(s), support member of the scanner, adjustable member (e.g., cover) of the scanner, or otherwise. In an embodiment, rather than or in addition to determining orientation of the physical position, a determination of a selectable switch, button, or other setting mechanism may be determined. For example, a timer switch that is set to turn on for an hour a night when a store or other venue is closed may cause the cleaner function to be initiated. In one embodiment, the processing unit may update the current orientation in memory with the detected orientation (or other setting). At step 1810, the code reader may scan the target area using a function corresponding to the detected orientation. The processing unit may direct components of the code reader to perform scanning functions corresponding with the detected orientation at step 1812. The functions may be functions described hereinabove with reference to FIGS. 1-6.

At step 1814, the processing unit may determine if the detected orientation corresponds with a cleaning function. If the orientation corresponds with the cleaning function, the processing unit may communicate to perform the cleaning function by emitting an anti-microbial illumination at step 1816. If the orientation does not correspond with the cleaning function, the code reader may scan the target area at step 1810 as described hereinabove. In an embodiment, the scanning and cleaning functions may be performed simultaneously.

One embodiment of a method for disinfecting a target area at a code reader may include determining if an orientation of a housing inclusive of a scanner for reading machine-readable indicia is an orientation corresponding with a cleaning function. In response to determining that the orientation of the housing is the orientation corresponding with the cleaning function, a cleaning function may be selected to cause an anti-microbial illumination to be emitted toward a target area of the scanner.

The anti-microbial illumination may emit a blue light having a wavelength between approximately 380 nanometers and approximately 470 nanometers. A determination if the orientation of the housing is the orientation corresponding with the cleaning function may include sensing a change in angular orientation of the housing. The housing may be supported by an adjustable arm having a first position for enabling the scanner to scan machine-readable indicia and a second position associated with the cleaning function.

A first level of anti-microbial illumination may be produced in response to determining that the housing is in an orientation not associated with the cleaning function. A second, higher level of anti-microbial illumination may be produced in response to determining that the housing is in the orientation corresponding with the cleaning function. The anti-microbial illumination may be produced in combination with the red light.

A shade configured to cover the target area and source of the anti-microbial illumination is deployed may be sensed, and the anti-microbial illumination may be caused to be at a power level higher than when the anti-microbial illumination is used for reading machine-readable indicia. A signal may be utilized to emit an anti-microbial light in response to deploy the reflective roller shade.

One embodiment of a method for disinfecting a surface at a code reader may include sensing an environmental factor at the code reader. In response to determining that the environmental factor is at a first value, the code reader may be configured to read machine-readable indicia. In response to determining that environmental factor is at a second value, an anti-microbial illumination may be caused to be emitted toward a target area of the scanner. In response to determining that the environmental factor is at the first value, the anti-microbial illumination may be caused to be emitted at a first power level. In response to determining that the environmental factor is at the second value, the anti-microbial illumination may be increased to be emitted at a second, higher power level.

The foregoing method descriptions and the process flow diagrams are provided merely as illustrative examples and are not intended to require or imply that the steps of the various embodiments must be performed in the order presented. As will be appreciated by one of skill in the art, the steps in the foregoing embodiments may be performed in any order. Words such as "then," "next," etc. are not intended to limit the order of the steps; these words are simply used to guide the reader through the description of the methods. Although process flow diagrams may describe the operations as a sequential process, many of the operations may be performed in parallel or concurrently. In addition, the order of the operations may be re-arranged. A process may correspond to a method, a function, a procedure, a subroutine, a subprogram, etc. When a process corresponds to a function, its termination may correspond to a return of the function to the calling function or the main function.

The various illustrative logical blocks, modules, circuits, and algorithm steps described in connection with the embodiments disclosed here may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to and/or in communication with another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the invention. Thus, the operation and behavior of the systems and methods were described without reference to the specific software code being understood that software and control hardware can be designed to implement the systems and methods based on the description here.

When implemented in software, the functions may be stored as one or more instructions or code on a non-transitory computer-readable or processor-readable storage medium. The steps of a method or algorithm disclosed here may be embodied in a processor-executable software module which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used here, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The previous description is of a preferred embodiment for implementing the invention, and the scope of the invention should not necessarily be limited by this description. The scope of the present invention is instead defined by the following claims.

What is claimed:

1. A code reader, comprising:
   a housing configured to be adjustably oriented, said housing including at least one orientation corresponding with a cleaning function;
   a scanner disposed within said housing, and configured to scan a machine-readable indicia in a target area;
   an illumination source configured to emit an anti-microbial illumination; and
   a processing unit in communication with said scanner and said illumination source, and configured to select the cleaning function responsive to determining that the housing is oriented according to the at least one orientation corresponding with the cleaning function to cause said illumination source to emit the anti-microbial illumination toward the target area to disinfect surfaces in the target area.

2. The code reader according to claim 1, wherein said scanner is configured to capture an image of the target area, and wherein said processing unit is further configured to determine the orientation of said housing based on the image of the target area.

3. The code reader according to claim 2, wherein said processing unit, in determining the orientation, is configured to identify known features disposed in a background portion of the image of the target area.

4. The code reader according to claim 1, wherein said housing is further configured to be supported by an adjustable arm having a first position for enabling said scanner to scan machine-readable indicia and a second position associated with the cleaning function, said processing unit being configured (i) to determine that the adjustable arm is in the second position, and (ii) to cause said illumination source to illuminate.

5. The code reader according to claim 1, wherein the anti-microbial illumination includes at least one of a blue light and an ultraviolet light.

6. The code reader according to claim 5, wherein the blue light includes a light emitting diode that emits light at a wavelength in a range between approximately 380 nanometers and approximately 470 nanometers.

7. The code reader according to claim 5, wherein said processing unit is further configured to emit the anti-microbial illumination in an asynchronous pattern.

8. The code reader according to claim 1, wherein said processing unit is further configured to emit the anti-microbial illumination in combination with a red light.

9. The code reader according to claim 1, further comprising a reflective roller shade configured to be positioned in a retracted position and a deployed position, the deployed position configured to cover the target area and illumination source.

10. The code reader according to claim 9, wherein said processing unit is further configured to receive a signal that the reflective roller shade is in the deployed position, and communicate a signal to said illumination source to emit the anti-microbial illumination in response to said reflective roller shade being in a deployed position.

11. A method for disinfecting a target area at a code reader, comprising:
determining if an orientation of a housing inclusive of a scanner for reading machine-readable indicia is an orientation corresponding with a cleaning function; and
in response to determining that the orientation of the housing is the orientation corresponding with the cleaning function, selecting a cleaning function to cause an anti-microbial illumination to be emitted toward a target area of the scanner.

12. The method according to claim 11, wherein emitting the anti-microbial illumination includes emitting a blue light having a wavelength between approximately 380 nanometers and approximately 470 nanometers.

13. The method according to claim 11, wherein determining if the orientation of the housing is the orientation corresponding with the cleaning function includes sensing a change in angular orientation of the housing.

14. The method according to claim 11, further comprising supporting the housing by an adjustable arm having a first position for enabling the scanner to scan machine-readable indicia and a second position associated with the cleaning function.

15. The method according to claim 11, further comprising:
producing a first level of anti-microbial illumination in response to determining that the housing is in an orientation not associated with the cleaning function; and
producing a second, higher level of anti-microbial illumination in response to determining that the housing is in the orientation corresponding with the cleaning function.

16. The method according to claim 11, further comprising producing the anti-microbial illumination in combination with the red light.

17. The method according to claim 11, further comprising:
sensing that a shade configured to cover the target area and source of the anti-microbial illumination is deployed; and
causing the anti-microbial illumination to be at a power level higher than when the anti-microbial illumination is used for reading machine-readable indicia.

18. The method according to claim 17, further comprising communicating a signal to all image sensors and scanners with anti-microbial illumination sources to emit the anti-microbial illumination in response to deploying the reflective roller shade.

19. The method according to claim 11, further comprising:
in response to determining that the environmental factor is at a first value, configuring the code reader to read machine-readable indicia; and
in response to determining that environmental factor is at a second value, causing the anti-microbial illumination to be emitted toward a target area of the scanner.

20. A method for disinfecting a surface at a code reader, comprising:
sensing an environmental factor at the code reader;
in response to determining that the sensed environmental factor is at a first value, configuring the code reader to read machine-readable indicia; and
in response to determining that the sensed environmental factor is at a second value, causing an anti-microbial illumination to be emitted toward a target area of the scanner.

21. The method according to claim 20, further comprising:
in response to determining that the environmental factor is at the first value, causing the anti-microbial illumination to be emitted at a first power level; and
in response to determining that the environmental factor is at the second value, increasing the anti-microbial illumination to be emitted at a second, higher power level.

* * * * *